US012778670B2

(12) United States Patent
Takahashi

(10) Patent No.: US 12,778,670 B2
(45) Date of Patent: Nov. 3, 2026

(54) MEDICAL DEVICE

(71) Applicant: TERUMO KABUSHIKI KAISHA, Tokyo (JP)

(72) Inventor: Yusuke Takahashi, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 728 days.

(21) Appl. No.: 18/164,019

(22) Filed: Feb. 3, 2023

(65) Prior Publication Data

US 2023/0248426 A1 Aug. 10, 2023

(30) Foreign Application Priority Data

Feb. 4, 2022 (JP) ................................ 2022-016304

(51) Int. Cl.
*A61B 18/14* (2006.01)
*A61B 18/00* (2006.01)

(52) U.S. Cl.
CPC *A61B 18/1492* (2013.01); *A61B 2018/00267* (2013.01); *A61B 2018/00595* (2013.01);
(Continued)

(58) Field of Classification Search
CPC ...... A61B 18/1492; A61B 2018/00267; A61B 2018/00595; A61B 2018/00946; A61B 2018/142; A61B 2018/0038
See application file for complete search history.

(56) References Cited

U.S. PATENT DOCUMENTS 5,645,076 A * 7/1997 Yoon .................. A61B 17/3417
604/165.01
10,849,638 B2 * 12/2020 Chu ....................... A61B 90/03
(Continued)

FOREIGN PATENT DOCUMENTS

JP H11-504234 A 4/1999
JP 2018-512965 A 5/2018
(Continued)

OTHER PUBLICATIONS

Office Action (Notice of Reasons for Refusal) issued on Apr. 30, 2025, in corresponding Japanese Patent Application No. 2022-016304 and machine English translation of the Office Action. (6 pages).

*Primary Examiner* — Beverly M Flanagan
*Assistant Examiner* — Abigail M Ziegler
(74) *Attorney, Agent, or Firm* — .Buchanan Ingersoll & Rooney PC

(57) ABSTRACT

A medical device that is capable of reducing release of a state in which an energy transmission element is pressed against a biological tissue due to an erroneous operation or a malfunction of an operation unit. The medical device includes an expandable body, a shaft portion connected to the expandable body, an energy transmission element provided in the expandable body, a housing connected to a proximal end portion of the shaft portion, a displacement shaft configured to compress the expandable body in an axial direction, an operation knob configured to operate the displacement shaft that is movable from a first position to a third position via a second position, with respect to the housing, and a lock portion configured to lock the operation knob at the second position.

20 Claims, 8 Drawing Sheets

(52) U.S. Cl.
CPC ............... *A61B 2018/00946* (2013.01); *A61B 2018/142* (2013.01)

(56) References Cited

U.S. PATENT DOCUMENTS

| | | | | |
|---|---|---|---|---|
| 2016/0074220 | A1* | 3/2016 | Ianchulev ............ | A61B 18/082 606/107 |
| 2019/0111238 | A1* | 4/2019 | Schultz ................ | A61B 5/6869 |
| 2020/0138445 | A1 | 5/2020 | Takahashi et al. | |
| 2021/0177506 | A1* | 6/2021 | Sheth ................. | A61B 18/1492 |

FOREIGN PATENT DOCUMENTS

| | | | |
|---|---|---|---|
| JP | 2019-519349 | A | 7/2019 |
| WO | 96/33752 | A2 | 10/1996 |
| WO | 2016/172640 | A1 | 10/2016 |
| WO | 2017/212334 | A1 | 12/2017 |
| WO | 2019/009254 | A1 | 1/2019 |
| WO | 2020094094 | A1 | 5/2020 |

* cited by examiner

MEDICAL DEVICE

CROSS-REFERENCES TO RELATED APPLICATIONS

This application claims priority to Japanese Application No. 2022-016304 filed on Feb. 4, 2022, the entire content of which is incorporated herein by reference.

TECHNOLOGICAL FIELD

The present disclosure generally relates to a medical device that includes an expandable body. The expandable body includes an energy transmission element that is inserted into a living body and that cauterizes a biological tissue.

BACKGROUND DISCUSSION

Chronic heart failure is a known heart disease. Chronic heart failure is broadly classified into a systolic heart failure and a diastolic heart failure, based on a cardiac function index. In a patient suffering from the diastolic heart failure, a myocardium is hypertrophied and increases in stiffness (hardness). Therefore, blood pressure in a left atrium increases and the pumping function of a heart is decreased. Accordingly, the patient shows a heart failure symptom such as a pulmonary edema. There is also a heart disease in which a blood pressure on a right atrium side increases due to pulmonary hypertension or the like, the pumping function of a heart is decreased, and thus heart failure symptoms are shown.

In recent years, for the patients suffering from heart failure, attention has been paid to a shunt treatment in which a shunt (through-hole) serving as an escape route for an increased atrial pressure is formed in an atrial septum, which can reduce heart failure symptoms. In the shunt treatment, the atrial septum is accessed using a transvenous approach method, and a through-hole having a desired size is formed. Examples of a medical device for performing such a shunt treatment for an atrial septum include a medical device described in International Patent Application No. WO 2020/094094.

The medical device described in International Patent Application No. WO 2020/094094 includes two expandable bodies disposed at a distal end portion of an elongated shaft, an electrode disposed on the expandable bodies, and an operation unit disposed at a proximal end portion of the shaft and capable of sandwiching a biological tissue by the two expandable bodies. The electrode can supply electric power from an electric power supply device (console) that can be connected to the medical device. A surgeon can operate the operation unit to sandwich the biological tissue using the two expandable bodies, and cauterize the sandwiched biological tissue by supplying electric power to the electrode disposed on the expandable bodies.

When energy is supplied without performing an operation of pressing the energy transmission element such as an electrode against the biological tissue, there is a risk that a thrombus is formed due to the energy transmission element being exposed to blood, or that an unintended part is damaged due to the energy transmission element. Such a risk also occurs when a state in which the energy transmission element is pressed against the biological tissue is released due to an erroneous operation or a malfunction of the operation unit before or during the output of energy from energy transmission element, in addition to a case in which a pressing operation is omitted unintentionally or erroneously.

SUMMARY

A medical device is disclosed that can reduce release of a state in which an energy transmission element is pressed against a biological tissue due to an erroneous operation or a malfunction of an operation unit.

A medical device is disclosed that includes: an expandable body that has a central axis and that is expandable and contractible in a radial direction; an elongated shaft portion connected to the expandable body; an energy transmission element provided along the expandable body; a housing connected to a proximal end portion of the shaft portion; an elongated displacement shaft configured to compress the expandable body in an axial direction; an operation knob configured to operate the displacement shaft that is movable from a first position to a third position via a second position substantially along an axis of the displacement shaft with respect to the housing; and a lock portion configured to lock the operation knob at the second position. The expandable body includes: a concave portion recessed inward in the radial direction at an intermediate portion in the axial direction; a first connection portion connected to the shaft portion; and a second connection portion facing the first connection portion with the concave portion interposed between second connection portion and the first connection portion in the axial direction and connected to the displacement shaft. The concave portion includes, in order to define a receiving space capable of receiving a biological tissue, a distal erected section, a proximal erected section, and a bottom section located on an innermost side in the radial direction and disposed between the distal erected section and the proximal erected section. The energy transmission element is disposed along any one of the distal erected section and the proximal erected section in a manner of facing the receiving space. The displacement shaft extends from inside the housing along the shaft portion and is connected to the second connection portion, and compresses the expandable body in the axial direction by relatively moving from an initial position to a compression position with respect to the shaft portion along the axial direction of the expandable body according to the movement of the operation knob from the first position to the second position. The distal erected section and the proximal erected section grip the biological tissue by the displacement of the displacement shaft from the initial position to the compression position. The operation knob includes: a knob body that protrudes from the housing, and that moves and operates the operation knob from the first position to the third position; an action portion movably disposed in the housing and connected to a proximal end portion of the displacement shaft, and configured to cause the displacement shaft to be displaced from the initial position to the compression position according to the movement and the operation of the operation knob; and a first engagement portion configured to move together with the action portion. The lock portion includes: a second engagement portion that is disposed in the housing and that is displaceable between an engagement position at which the second engagement portion is engaged with the first engagement portion of the operation knob located at the second position, and a release position at which the engagement with the first engagement portion is released; a release button that is exposed from the housing and that causes the second engagement portion to be displaced from the engagement position to the release position; and a flexible deformable portion that connects the release button and the second engagement portion to each other. When the release button is pressed in a state in which the operation knob is located at the second position, the flexible deformable portion is deformed to prevent displacement of the second engagement portion engaged with the first engagement portion from the engagement position to the release position, and when the release button is pressed in a state in which the operation knob is located at the third position, the second engagement portion is displaced from the engagement position to the release position and an engagement state between the first engagement portion and the second engagement portion is releasable.

In the medical device implemented as described above, when the operation knob is not moved from the second position to the third position, even if the release button is pressed, the second engagement portion cannot be displaced from the engagement position to the release position, and the lock portion that locks the operation knob at the second position cannot be released. Therefore, the medical device can reduce the release of the state in which the energy transmission element is pressed against the biological tissue due to an erroneous operation or a malfunction of the operation unit before or during the output of energy from the energy transmission element in a state in which the expandable body is compressed and the biological tissue is gripped.

The flexible deformable portion may have an elongated shape projected on a plane including the axis of the displacement shaft, and may be pivotally disposed in the housing such that an inclination amount of the flexible deformable portion with respect to the axis of the displacement shaft changes. The release button and the second engagement portion may be disposed at both ends of the flexible deformable portion in a direction along the axis of the displacement shaft. The release button is pressed, so that an inclination of the flexible deformable portion with respect to the axis of the displacement shaft may be increased, and the second engagement portion may be displaced from the engagement position to the release position. Accordingly, the second engagement portion can be displaced from the engagement position to the release position by the inclination of the flexible deformable portion with respect to the housing caused by pressing the release button. Further, it is also possible that, by flexing the flexible deformable portion and absorbing the displacement generated by the release button using the flexible deformable portion, the second engagement portion is not displaced from the engagement position to the release position even if the release button is pressed.

The flexible deformable portion may include a pivot shaft portion protruding in a direction substantially perpendicular to the axis of the displacement shaft at an intermediate portion in the direction along the axis of the displacement shaft. The housing may include a bearing portion receiving the pivot shaft portion. Accordingly, by rotating the flexible deformable portion around the pivot shaft portion received in the bearing portion, an operation that the release button is pressed can be converted into an operation that the second engagement portion is displaced from the engagement position to the release position.

The medical device may include a biasing portion that is elastically deformable along the axis of the displacement shaft so as to bias the first engagement portion of the operation knob located at the second position toward the second engagement portion. Accordingly, since the second engagement portion is pressed against the first engagement portion by a biasing force of the biasing portion, the second engagement portion can be prevented, by a frictional force, from being displaced from the engagement position to the release position.

The action portion of the operation knob may be connected to a proximal end portion of the displacement shaft via the biasing portion. Accordingly, since a force for gripping the biological tissue by the expandable body can be appropriately adjusted by the biasing portion, it is possible to prevent the gripping force from becoming excessive, and to reduce damage to the biological tissue.

The operation knob may include a hook portion engageable with the second engagement portion, and when the operation knob is located at the second position, the hook portion may be hooked on the second engagement portion to prevent the displacement of the second engagement portion from the engagement position to the release position, and when the operation knob is located at the third position, the hook portion may be separated from the second engagement portion. Accordingly, when the operation knob is located at the second position, the second engagement portion can be reliably prevented from being displaced from the engagement position to the release position by the hook portion.

The hook portion may be a convex portion protruding from the first engagement portion toward the second engagement portion. Accordingly, the hook portion, which is a convex portion, can be firmly engaged with the second engagement portion, and can be easily separated from the second engagement portion by the operation knob moving to the third position, whereby the engagement can be released.

The operation knob may include a third engagement portion that engages with the second engagement portion when the operation knob is located at the first position to prevent the movement of the operation knob from the first position to the second position, and the engagement between the second engagement portion and the third engagement portion may be releasable by pressing the release button. Accordingly, it is possible to prevent the operation knob from unintentionally moving from the first position to the second position due to an erroneous operation or a malfunction. Therefore, the unintentional expansion of the expandable body can be reduced, and the safety can be improved. In addition, reduction in diameter of the expandable body, which can be reduced in the diameter when the operation knob is located at the first position, can be prevented from being hindered by the displacement shaft unintentionally moving toward the proximal side, and the safety can be improved.

The first connection portion of the expandable body may be located at a proximal side with respect to the second connection portion. The displacement shaft may compress the expandable body in the axial direction by pulling the second connection portion in a proximal direction according to a movement from the initial position to the compression position located at the proximal side with respect to the initial position. The operation knob may cause the displacement shaft to move from the initial position to the compression position according to a movement from the first position to the second position located at the proximal side with respect to the first position. The first engagement portion may be a first convex portion that protrudes from the action portion toward the direction substantially perpendicular to the axis of the displacement shaft and that has a distal surface. The second engagement portion may be a second convex portion that protrudes from the flexible deformable portion toward the direction substantially perpendicular to the axis of the displacement shaft to engage with the distal surface of the first convex portion. Accordingly, by engaging the second convex portion provided in the lock portion with the distal surface of the first convex portion provided in the operation knob that is moved from the first position to the second position so as to compress the expansion body, it is possible to effectively maintain a state in which the expandable body is compressed.

The first convex portion may have an inclined surface inclined such that a protruding amount from the action portion gradually decreases toward a proximal end of the first convex portion. The distal surface of the first convex portion may be a surface substantially perpendicular to the axis of the displacement shaft. The second engagement portion may have a proximal surface substantially perpendicular to the axis of the displacement shaft engaged with the distal surface of the first convex portion. Accordingly, when the operation knob moves from the first position to the second position, the inclined surface of the first convex portion can come into contact with the second engagement portion and smoothly move over the second engagement portion, and when the operation knob reaches the second position, the distal surface of the first convex portion can engage with the second engagement portion to prevent the operation knob from returning to the first position.

A medical device is disclosed comprising: an expandable body having a central axis and configured to be expandable and contractible in a radial direction; an elongated shaft portion configured to be connected to the expandable body; an energy transmission element provided along the expandable body; a housing configured to be connected to a proximal end portion of the shaft portion; an elongated displacement shaft configured to compress the expandable body in an axial direction; an operation knob configured to operate the displacement shaft that is configured to be movable from a first position to a third position via a second position substantially along an axis of the displacement shaft with respect to the housing; a lock portion configured to lock the operation knob at the second position; the displacement shaft extends from inside the housing along the shaft portion and is connected to the expandable body, and is configured to compress the expandable body in the axial direction by relatively moving from an initial position to a compression position with respect to the shaft portion along the axial direction of the expandable body according to the movement of the operation knob from the first position to the second position; and wherein the operation knob includes a knob body that protrudes from the housing, and configured move and operate the operation knob from the first position to the third position, an action portion configured to be movably disposed in the housing and connected to a proximal end portion of the displacement shaft, and configured to cause the displacement shaft to be displaced from the initial position to the compression position according to the movement and the operation of the operation knob, and a first engagement portion configured to move together with the action portion.

An operation unit is disclosed for use in cauterization of a biological tissue, the operation unit comprising: a housing; an operation knob configured to operate a displacement shaft that is configured to be movable from a first position to a third position via a second position substantially along an axis of the displacement shaft with respect to the housing; a lock portion configured to lock the operation knob at the second position; and wherein the operation knob includes a knob body that protrudes from the housing, and configured move and operate the operation knob from the first position to the third position, an action portion configured to be movably disposed in the housing and connected to a proximal end portion of the displacement shaft, and configured to cause the displacement shaft to be displaced from the initial position to the compression position according to the movement and the operation of the operation knob, and a first engagement portion configured to move together with the action portion.

BRIEF DESCRIPTION OF THE DRAWINGS

FIG. 3A is a longitudinal sectional view, and FIG. 3B is a sectional view taken along a line A-A of FIG. 3A.

FIG. 5A illustrates a state in which the operation knob starts to move from a first position to a proximal side, FIG. 5B illustrates a state in which the operation knob reaches a second position, and FIG. 5C illustrates a state in which the release button is pressed when the operation knob is located at the second position.

FIG. 6A illustrates a state in which the operation knob moves to a third position and the release button is pressed, and FIG. 6B illustrates a state in which the operation knob returns to the first position.

FIG. 13A illustrates a state in which the operation knob is located at the second position, and FIG. 13B illustrates a state in which the operation knob is located at the third position and the release button is pressed.

FIG. 14A is a plan view before a biological tissue is gripped by an expandable body, and FIG. 14B is a plan view after the biological tissue is gripped by the expandable body.

DETAILED DESCRIPTION

Figure 1:
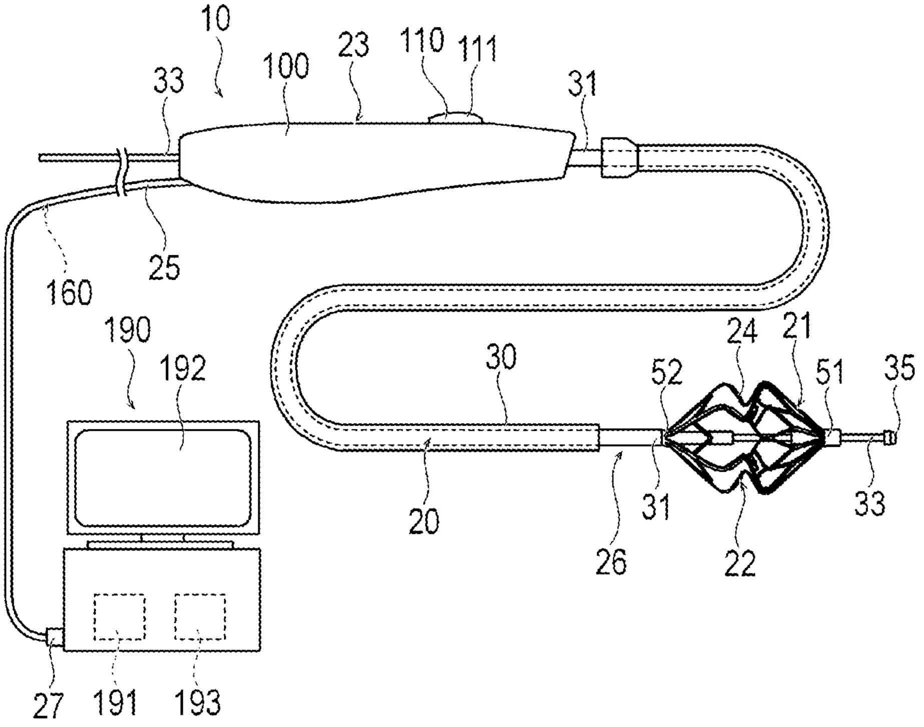
FIG. 1 is a side view illustrating an overall configuration of a medical system according to an embodiment.

Set forth below with reference to the accompanying drawings is a detailed description of embodiments of a medical device that includes an expandable body. The expandable body includes an energy transmission element that is inserted into a living body and that cauterizes a biological tissue. Note that since embodiments described below are preferred specific examples of the present disclosure, although various technically preferable limitations are given, the scope of the present disclosure is not limited to the embodiments unless otherwise specified in the following descriptions. In the drawings, the same or corresponding parts are denoted by the same reference numerals. In the description of the present embodiment, the description of the same or corresponding parts will be omitted or simplified as appropriate. For convenience of description, dimensional ratios in the drawings may be exaggerated and may be different from actual ratios. In addition, in the present description, a side where a medical device 10 is inserted into a body lumen is referred to as a "distal side", and a side where the medical device 10 is operated is referred to as a "proximal side". In the present description, the description "X to Y" indicating a range includes X and Y, and means "X or more and Y or less".

Figure 7:
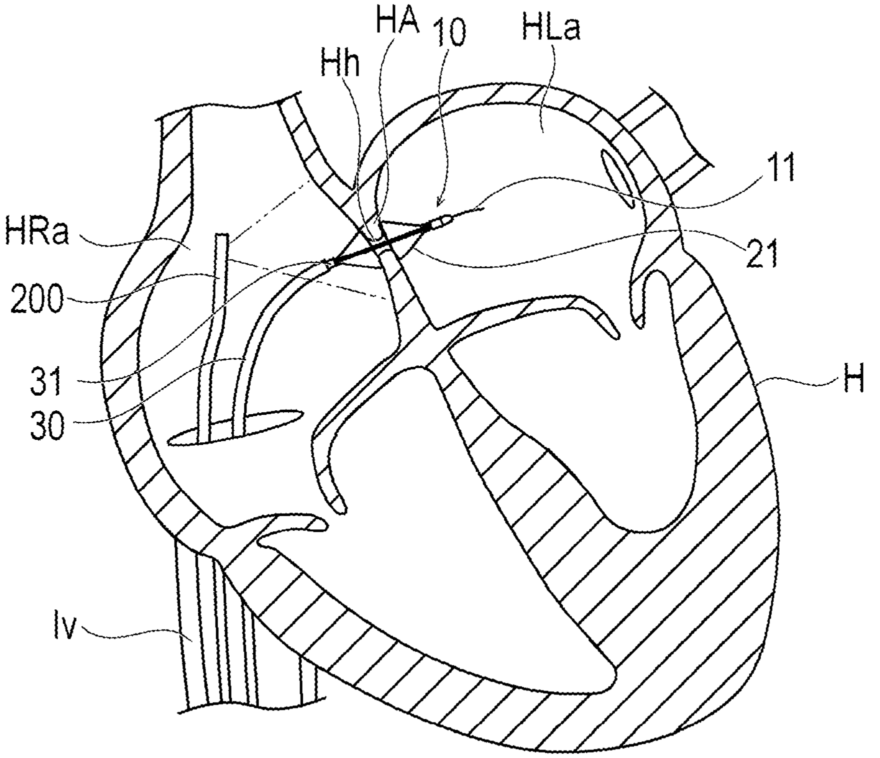
FIG. 7 is a schematic diagram schematically illustrating a state in which an expandable body is disposed in a through-hole of an atrial septum.

As illustrated in FIG. 7, the medical device 10 according to the present embodiment can perform a maintenance treatment of maintaining a size of a through-hole Hh that is formed in an atrial septum HA, which is a biological tissue of a heart H of a patient, and is expanded by a balloon.

Figure 2:
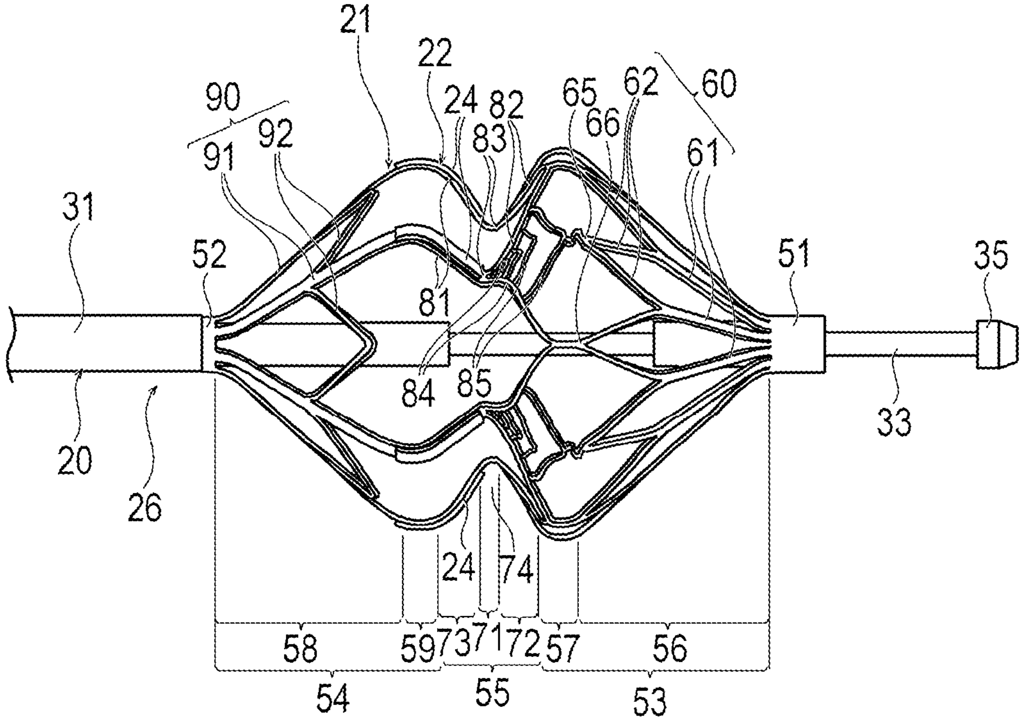
FIG. 2 is a side view illustrating a distal end portion of a medical device.

As illustrated in FIGS. 1 and 2, the device according to the present embodiment is the medical device 10 that is inserted into a living body and that cauterizes a biological tissue, and is operated by electric power supplied from an electric power supply device 190.

The medical device 10 includes an elongated portion 20 that extends from a proximal end to a distal end, an expandable body 21 provided at a distal end portion of the elongated portion 20, an energy transmission element 22 provided with a plurality of electrodes 24 along the expandable body 21, an operation unit 23 connected to a proximal end portion of the elongated portion 20, a connection terminal 27 connectable to the electric power supply device 190, and a connection cable 25 extending from the operation unit 23 to the connection terminal 27.

The elongated portion 20 includes a shaft portion 31 that holds the expandable body 21 at the distal end portion, an outer tube 30 that houses the shaft portion 31, a displacement shaft 33, and a pulling portion 35 that is fixed to a distal end of the displacement shaft 33.

The shaft portion 31 is an elongated tube extending from the operation unit 23 to the expandable body 21. A proximal end portion of the shaft portion 31 is fixed to a distal end portion of the operation unit 23. A distal end portion of the shaft portion 31 is fixed to a proximal end portion of the expandable body 21.

The outer tube 30 is an elongated tube that covers the shaft portion 31, and is movable forward and backward in an axial direction (a direction of an axis of the elongated portion 20) with respect to the shaft portion 31. The expandable body 21 contracted in a radial direction can be housed in the outer tube 30 in a state in which the outer tube 30 moves to a distal side of the elongated portion 20. The radial direction is a direction orthogonal to an axis of the shaft portion 31. The surgeon can cause the expandable body 21 to be exposed (i.e., removed) from the outer tube 30 and to expand in the radial direction by moving the outer tube 30 in a state in which the expandable body 21 is housed toward the proximal side.

The displacement shaft 33 is an elongated tube disposed (or located) inside the shaft portion 31, and is movable forward and backward with respect to the shaft portion 31 in the axial direction. The displacement shaft 33 protrudes from a distal end of the shaft portion 31 toward the distal side, and protrudes from a distal end of the expandable body 21 toward the distal side. A distal end portion of the displacement shaft 33, which is located at the distal side with respect to the expandable body 21, is fixed to the pulling portion 35. A proximal end portion of the displacement shaft 33 extends from a proximal side of the operation unit 23 such that the proximal end portion of the displacement shaft 33 extends to a more proximal side of the medical device 10 than the operation unit 23. A guide wire lumen is formed along the axial direction inside the displacement shaft 33, and a guide wire 11 (see FIGS. 8 to 10) can be inserted through the guide wire lumen of the displacement shaft 33. The displacement shaft 33 can compress the expandable body 21 in the axial direction by being relatively displaced from an initial position (see FIGS. 3A and 3B) to a compression position (see FIG. 5B) with respect to the shaft portion 31 along an axial direction of the expandable body 21.

The pulling portion 35 can be an annular member fixed to an outer peripheral surface of the distal end portion of the displacement shaft 33, and protrudes outward in the radial direction from the outer peripheral surface of the displacement shaft 33. The pulling portion 35 is not fixed to the expandable body 21. An outer diameter of the pulling portion 35 is larger than an inner diameter of the distal end portion of the expandable body 21. Therefore, the pulling portion 35 can abut on the distal end portion of the expandable body 21 from the distal side, pull the expandable body 21 toward a proximal direction, and apply a compressive force, which compresses along an axial direction of the shaft portion 31, to the expandable body 21.

As illustrated in FIGS. 1, 3A, 3B, and FIG. 4, the operation unit 23 includes a housing 100 that can be gripped by the surgeon, an operation knob 110 that is allowed to be moved along the axis of the displacement shaft 33 by the surgeon, a biasing portion 120 that transmits the movement of the operation knob 110 to the displacement shaft 33, a lock portion 140 that locks the operation knob 110 at a predetermined position, an electric wire 160 that transmits electric power from the electric power supply device 190 to the electrodes 24, and a shaft connecting portion 180 that connects the shaft portion 31 to the housing 100.

The housing 100 can include a guide rail 101 that holds the operation knob 110 in a manner of being linearly slidable along the axis of the displacement shaft 33, a knob opening 102 that causes a part of the operation knob 110 to be exposed outside, a button opening 103 that causes a release button 141 provided on the lock portion 140 to be exposed outside, and a bearing portion 104 to which the lock portion 140 is rotatably connected. The knob opening 102 and the button opening 103 open in a direction substantially orthogonal to the axis of the displacement shaft 33. The knob opening 102 has a size that allows the operation knob 110 to be movable along the axis of the displacement shaft 33. The button opening 103 is disposed on a distal side of the knob opening 102.

The operation knob 110 is slidable with respect to the housing 100 along the axis of the displacement shaft 33. The operation knob 110 can cause the displacement shaft 33 to move from the initial position to the compression position by moving from the first position (see FIGS. 3A and 3B) to a second position (see FIG. 5B) at the proximal side with respect to the first position. The operation knob 110 can further move from the second position to a third position (see FIG. 6A) at the proximal side with respect to the second position. The operation knob 110 includes a knob body 111 that is exposed outside from the knob opening 102 of the housing 100 so that the surgeon can operate the knob body 111, an action portion 114 that is movably disposed in the housing 100 and is connected to the proximal end portion of the displacement shaft 33, and that causes the displacement shaft 33 to be displaced from the initial position to the compression position according to the movement and the operation of the operation knob 110, a sliding portion 112 that comes into contact with the guide rail 101 in a manner of being linearly slidable along the axis of the displacement shaft 33 inside the housing 100, and a stopper 115 that can abut on a proximal surface of a ring-shaped fixing member 170 fixed to the displacement shaft 33.

The operation knob 110 can further include a first engagement portion 116 and a third engagement portion 117 that can be engaged with a second engagement portion 142 of the lock portion 140 to be described later in detail. The first engagement portion 116 and the third engagement portion 117 are displaced together with the knob body 111 and the action portion 114, and the first engagement portion 116 is disposed at the distal side with respect to the third engagement portion 117.

The first engagement portion 116 can be a first convex portion 116A that protrudes from the action portion 114 in a direction substantially perpendicular to the axis of the displacement shaft 33 and that has a distal surface 116B and an inclined surface 116C. The distal surface 116B can be a surface substantially perpendicular to the axis of the displacement shaft 33. The inclined surface 116C can be inclined such that a protruding amount from the action portion 114 gradually decreases toward a proximal end of the first convex portion 116A.

The third engagement portion 117 is disposed at the proximal side with respect to the first engagement portion 116 along the axis of the displacement shaft 33. The third engagement portion 117 can be a third convex portion 117A that protrudes from the action portion 114 in the direction substantially perpendicular to the axis of the displacement shaft 33, and that has a proximal surface 117B and an inclined surface 117C. The proximal surface 117B can be a surface substantially perpendicular to the axis of the displacement shaft 33. The inclined surface 117C can be inclined such that the protruding amount from the action portion 114 gradually decreases toward a distal end of the third convex portion 117A.

The action portion 114 is a portion that causes a pulling force toward the proximal direction to act on the displacement shaft 33 via the biasing portion 120. Since the action portion 114 is connected to the proximal end portion of the displacement shaft 33 via the biasing portion 120, the operation knob 110 moves from the first position to the second position along an axial direction of the displacement shaft 33, so that the action portion 114 can press the displacement shaft 33 via the biasing portion 120 and cause the displacement shaft 33 to move from the initial position to the compression position. Further, the action portion 114 can move from the second position to the third position toward the proximal side against the biasing force of the biasing portion 120.

The stopper 115 is disposed at the proximal side with respect to the action portion 114. The stopper 115 abuts on the proximal surface of the fixing member 170 fixed to the displacement shaft 33, thereby limiting the displacement shaft 33 from moving more than necessary toward the proximal direction with respect to the operation knob 110.

Figure 3A:
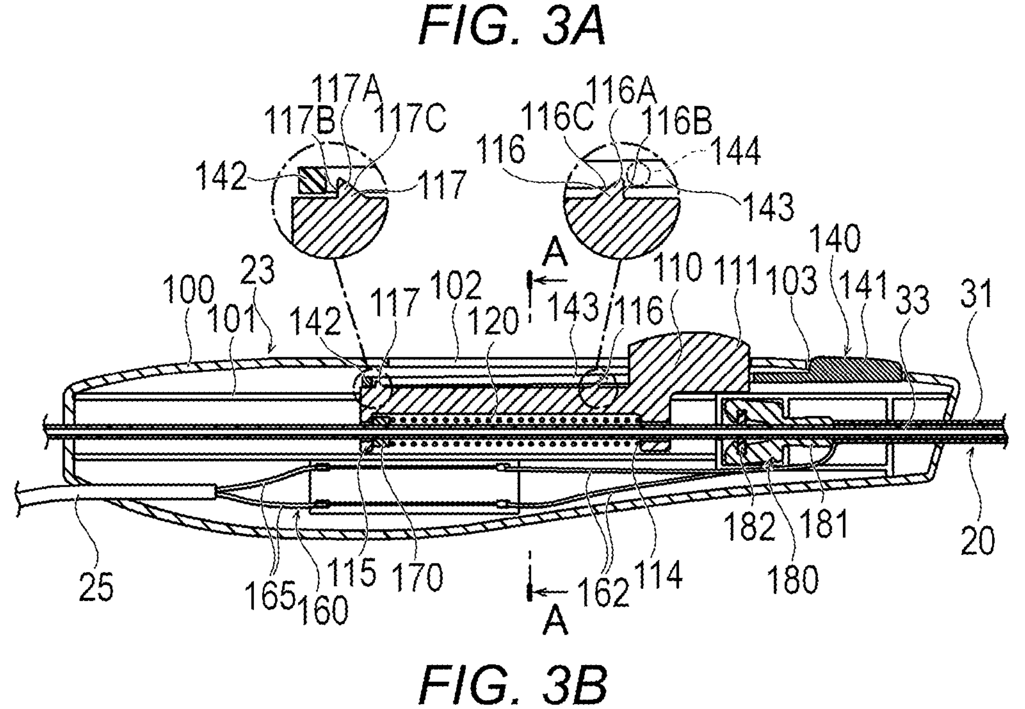
FIGS. 3A and 3B are diagrams illustrating an inside of an operation unit before an operation knob is operated.
Figure 3B:
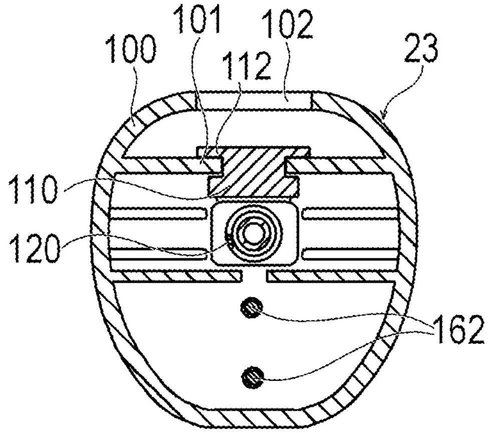
Figure 4:
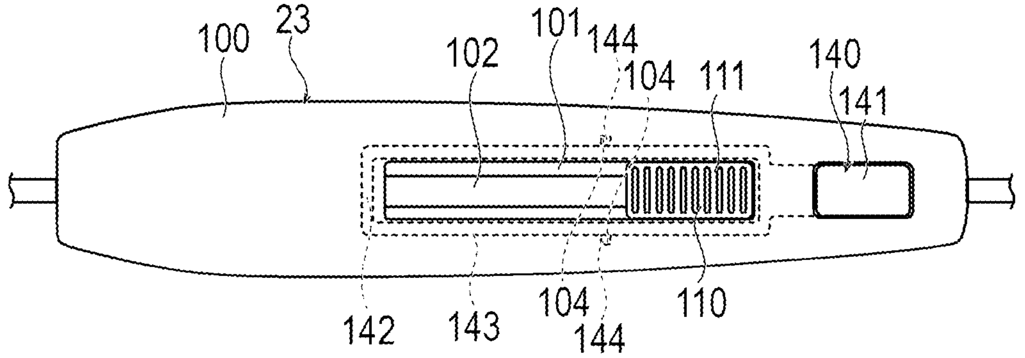
FIG. 4 is a top view of the operation unit.

As illustrated in FIGS. 3A, 3B, and 4, the lock portion 140 includes the release button 141 that can be pressed and operated by the surgeon, the second engagement portion 142 that is engageable with the first engagement portion 116 and the third engagement portion 117, a flexible deformable portion 143 that connects the release button 141 and the second engagement portion 142, and a pivot shaft portion 144 that is rotatably connected to the housing 100.

The release button 141 is located at a distal end portion of the lock portion 140, and is exposed to the outside from the inside of the housing 100 through the button opening 103 of the housing 100. The release button 141 may be biased from the inside toward the outside of the housing 100 by a spring member or the like.

The second engagement portion 142 is located at a proximal end portion of the lock portion 140, and is disposed inside the housing 100. The release button 141 is pressed and the lock portion 140 rotates around the pivot shaft portion 144, so that the second engagement portion 142 is movable in the direction substantially orthogonal to the axis of the displacement shaft 33.

The flexible deformable portion 143 has an elongated shape projected on a plane including the axis of the displacement shaft 33, has flexibility, and is pivotally disposed inside the housing 100 such that an inclination amount with respect to the axis of the displacement shaft 33 changes. The release button 141 and the second engagement portion 142 are disposed at both ends of the flexible deformable portion 143 in a direction along the axis of the displacement shaft 33. The flexible deformable portion 143 pivots such that the inclination with respect to the axis of the displacement shaft 33 is changed when the surgeon presses the release button 141 (see FIGS. 5A and 6A).

The pivot shaft portion 144 protrudes from the flexible deformable portion 143 located between the release button 141 and the second engagement portion 142 toward a direction that is orthogonal to the axis of the displacement shaft 33 and that is orthogonal to a direction in which the second engagement portion 142 and the release button 141 are displaceable. The pivot shaft portion 144 is rotatably held at the bearing portion 104 formed in the housing 100. When the surgeon presses the release button 141 exposed from the button opening 103, the lock portion 140 pivots around the pivot shaft portion 144, the release button 141 is pushed into the button opening 103, and the second engagement portion 142 moves from the release position to a displaced position (see FIGS. 5A and 6A).

The release button 141 is pressed and the lock portion 140 pivots, so that the second engagement portion 142 is displaceable toward the direction substantially orthogonal to the axis of the displacement shaft 33. As illustrated in FIG. 3A, the second engagement portion 142 is disposed at, in a manner of being separated from the proximal surface 117B at a relatively small distance, a proximal side of the proximal surface 117B of the third engagement portion 117 in the operation knob 110 located at the first position. In a state in which the release button 141 is not pressed, when the operation knob 110 moves from the first position toward the proximal side, the second engagement portion 142 can come into contact with the proximal surface 117B of the third engagement portion 117 in the operation knob 110, and can help prevent the operation knob 110 from moving toward the proximal side.

The second engagement portion 142 is displaceable between an engagement position at which the second engagement portion 142 can engage with the distal surface 116B of the first engagement portion 116 in the operation knob 110 located at the second position, as illustrated in FIG.

Figure 6A:
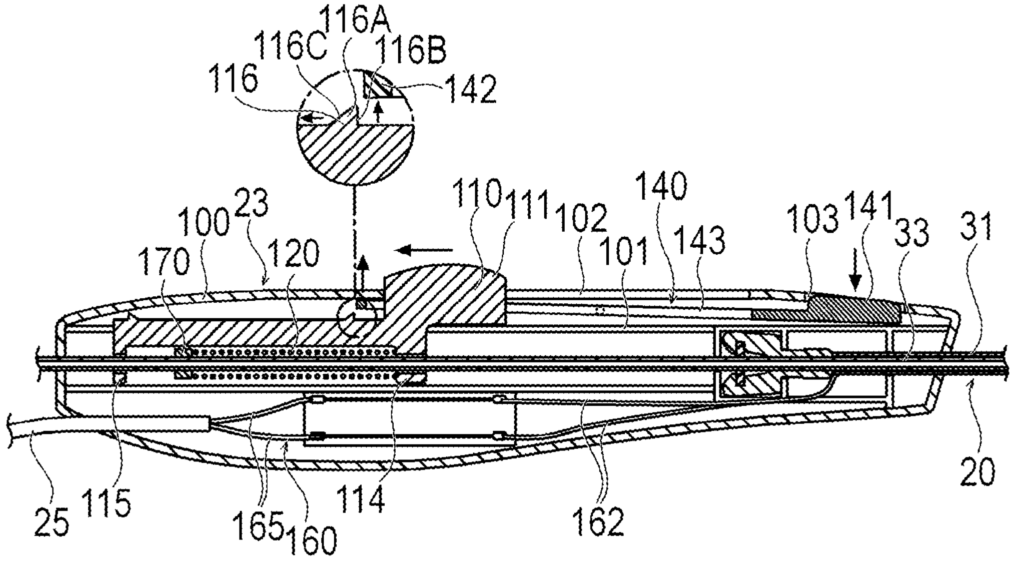
FIGS. 6A and 6B are longitudinal sectional views illustrating the inside of the operation unit.

5B, and a release position at which the engagement with the first engagement portion 116 is released, as illustrated in FIG. 6A.

As illustrated in FIGS. 3A and 3B, the biasing portion 120 is disposed between the operation knob 110 and the displacement shaft 33 in order to adjust the pulling force transmitted from the operation knob 110 to the displacement shaft 33. The biasing portion 120 can be a coil spring surrounding the displacement shaft 33. The biasing portion 120 can elastically expand and contract along the axial direction of the displacement shaft 33. A distal end of the biasing portion 120 can abut on a proximal surface of the action portion 114 in the operation knob 110. A proximal end of the biasing portion 120 can abut on a distal surface of the fixing member 170 fixed to the displacement shaft 33.

As illustrated in FIGS. 1, 3A, and 3B, the electric wire 160 includes connecting electric wire portions 165 that extend from the connection terminal 27 connectable to the electric power supply device 190 to the inside of the housing 100 through the connection cable 25, and electric wire main bodies 162 that are connected to the connecting electric wire portions 165 inside the housing 100 and that extend to the energy transmission element 22 along the shaft portion 31.

As illustrated in FIGS. 3A and 3B, the shaft connecting portion 180 can include a holding portion 181 that is fixed and held inside the housing 100, and a seal member 182 that is disposed inside the holding portion 181. The holding portion 181 can be a substantially cylindrical member that is connected in close contact with a proximal end of the shaft portion 31. The seal member 182 can be an annular member that is disposed inside the holding portion 181 at the proximal side with respect to the shaft portion 31 and that is slidably in contact with the outer peripheral surface of the displacement shaft 33. The seal member 182 can help prevent blood or the like from flowing into the housing 100 from between the shaft portion 31 and the displacement shaft 33.

As illustrated in FIGS. 1 and 2, the expandable body 21 can include a force receiving portion 51 disposed at the distal end of the expandable body 21, a proximal end connection portion 52 disposed at the proximal end of the expandable body 21, a second connection portion 53 connected to the force receiving portion 51, a first connection portion 54 connected to the proximal end connection portion 52, and concave portions 55 formed between the second connection portion 53 and the first connection portion 54.

The force receiving portion 51 can be annular, and can receive a force from the pulling portion 35 disposed on the distal side toward the proximal direction. The proximal end connection portion 52 can be annular, and is fixed to the distal end portion of the shaft portion 31.

The second connection portion 53 can be deformable in a flexible manner. The second connection portion 53 can include a distal extension portion 56 extending outward in the radial direction from the force receiving portion 51 toward the proximal direction, and a distal apex portion 57 disposed on a proximal side of the distal extension portion 56 and curved outward in a protrusive manner in the radial direction.

The second connection portion 53 includes a plurality of distal strut structures 60 extending outward in the radial direction from the force receiving portion 51 toward the proximal direction to form the distal extension portion 56. The plurality of distal strut structures 60 can be arranged at substantially equal intervals in a circumferential direction of the expandable body 21 at the time of expansion.

Each of the distal strut structures 60 can include a first strut 61 extending from the force receiving portion 51 toward the proximal direction, and a second strut 62 extending from a proximal end of the first strut 61 toward the proximal direction and connected to the distal apex portion 57.

Each of the first struts 61 extends from the force receiving portion 51 substantially parallel to an axis of the expandable body 21 when viewed from the outside in the radial direction. Each of the second struts 62 branches into two branches in a manner of extending toward the circumferential direction of the expandable body 21 while going from the proximal end of each of the first struts 61 toward the proximal direction, and joins at a first junction portion 65 or a second junction portion 66. The first junction portions 65 and the second junction portions 66 are alternately arranged at substantially equal intervals in the circumferential direction of the expandable body 21 at the time of expansion.

Each of the first junction portions 65 is connected to the distal apex portion 57 disposed in the same phase as the electrodes 24 in the circumferential direction of the expandable body 21. Each of the second junction portions 66 is connected to the distal apex portion 57 disposed in different phases with respect to the electrodes 24 in the circumferential direction of the expandable body 21.

The first connection portion 54 is deformable in a flexible manner. The first connection portion 54 includes a proximal extension portion 58 extending outward in the radial direction from the proximal end connection portion 52 toward a distal direction, and a proximal apex portion 59 disposed on a distal side of the proximal extension portion 58 and curved outward in a protrusive manner in the radial direction.

The proximal extension portion 58 includes a plurality of proximal strut structures 90. The proximal strut structures 90 can be disposed in the same phase as a plurality of electrode disposing portions 81 in the circumferential direction of the expandable body 21. Each of the proximal strut structures 90 can include a plurality of third struts 91 extending, substantially parallel to the axis of the expandable body 21 when viewed from the outside in the radial direction, from the distal end portion of the shaft portion 31 to the proximal apex portion 59, and a plurality of secondary struts 92 connecting the third struts 91 adjacent to each other in the circumferential direction. Each of the secondary struts 92 is connected to the two third struts 91 adjacent to each other in the circumferential direction. The secondary struts 92 can be bent. Therefore, even in a case in which a distance between the two third struts 91 adjacent to each other when the expandable body 21 is expanded becomes long, the two third struts 91 can be continuously supported while the secondary struts 92 are deformed into a shape close to a straight line. Therefore, the expandable body 21 can expand while extending the third struts 91 at substantially equal intervals by a compressive force applied by the displacement shaft 33.

The concave portions 55 are deformable in a flexible manner. When the expandable body 21 is expanded, the concave portions 55 are recessed inward in the radial direction, and extend to connect the proximal apex portion 59 and the distal apex portion 57. The concave portions 55 define a receiving space 74 capable of receiving a biological tissue of a living body when the expandable body 21 is expanded.

Each of the concave portions 55 includes a bottom section 71 located on the innermost side in the radial direction, a distal erected section 72 extending outward in the radial direction from a distal end of the bottom section 71 to the distal apex portion 57, and a proximal erected section 73 extending outward in the radial direction from a proximal end of the bottom section 71 to the proximal apex portion 59.

It is preferable that intervals between the proximal erected sections 73 and the distal erected sections 72 are slightly larger on the outside than those on the inside of the radial direction in the axial direction at the time of expansion of the expansion portion. Accordingly, it is relatively easy to dispose the biological tissue from the outside in the radial direction between the proximal erected sections 73 and the distal erected sections 72.

The concave portions 55 have a plurality of concave strut structures 80 arranged in the circumferential direction. Each of the plurality of concave strut structures 80 can include the electrode disposing portions 81 disposed on the proximal erected sections 73 and a plurality of facing portions 82 disposed on the distal erected sections 72, and further includes a plurality of bottom section connecting portions 83 each connecting one of the electrode disposing portions 81 and one of the facing portions 82, which constitute a pair, to the bottom sections 71.

The electrode disposing portions 81 are arranged at substantially equal intervals in the circumferential direction of the expandable body 21. The facing portions 82 are arranged at substantially equal intervals in the circumferential direction of the expandable body 21. The plurality of bottom section connecting portions 83 are arranged at substantially equal intervals in the circumferential direction of the expandable body 21.

The facing portions 82 each face a respective one of the electrodes 24 at the time of expansion of the expandable body 21. Each of the facing portions 82 includes a plurality of distal erected struts 84 that branch into two branches while spreading toward the distal direction in a manner of extending substantially along the circumferential direction of the expandable body 21 from distal ends of the bottom section connecting portions 83, and a plurality of back contact portions 85. The plurality of back contact portions 85 connect the two distal erected struts 84 branched from each of the bottom section connecting portions 83. The back contact portions 85 are arranged side by side from a side close to the bottom sections 71 to a side close to the distal apex portion 57. Each of the back contact portions 85 is curved such that a part between both ends connected to the two distal erected struts 84 protrudes toward the distal apex portion 57. Each of the back contact portions 85 is more likely to bend on the side close to the distal apex portion 57 with both the ends connected to the distal erected struts 84 as supporting points. Therefore, the back contact portions 85 can be bent by a force toward the distal side. The force is received from the electrodes 24 disposed on the proximal erected sections 73. Therefore, the biological tissue sandwiched between the electrodes 24 and the back contact portions 85 can be brought into close contact with the electrodes 24. Of the back contact portions 85 forming the facing portions 82, the back contact portion 85 closest to the distal apex portion 57 is connected to the distal apex portion 57 at a part protruding toward the distal apex portion 57. The number of the back contact portions 85 forming the facing portions 82 is not particularly limited.

The energy transmission element 22 includes the plurality of electrodes 24. Each of the electrodes 24 is disposed on a surface of a respective one of the electrode disposing portions 81 that forms an inner side of the concave portion 55. The electrodes 24 are disposed in relatively close contact with the surfaces of the electrode disposing portions 81 that form the inner side of the concave portions 55. A surface of at least a part of the electrodes 24, which faces the receiving space 74 at the time of expansion, has a convex curved surface shape. The surface of the electrodes 24 that faces the receiving space 74 at the time of expansion may have a planar shape.

The electrodes 24 are disposed on surfaces facing a distal side of the proximal erected sections 73 at the time of expansion of the expandable body 21. Since the electrodes 24 are provided on the proximal erected sections 73, when the concave portions 55 hold the atrial septum HA, energy from the electrodes 24 is transmitted from a right atrium side to the atrial septum HA. When the electrodes 24 are provided on the distal erected sections 72, the energy from the electrodes 24 is transmitted from a left atrium side to the atrial septum HA.

The electrodes 24 can be implemented by, for example, bipolar electrodes that receive electric power from the electric power supply device 190. In the case of the electrodes 24 being bipolar electrodes, energization is performed between the electrodes 24 disposed in the electrode disposing portions 81.

Further, the electrodes 24 may be implemented as monopolar electrodes. In the case of the electrodes 24 being monopolar electrodes, energization is performed with a counter electrode plate prepared outside a body. In addition, the electrodes 24 may be heating elements (electrode tips) that receive high-frequency electric energy from an energy supply apparatus and that generate heat. Further, the energy transmission element 22 may be implemented as an energy transmission element capable of applying energy to the through-hole Hh, such as an element that provides heating and cooling operation using microwave energy, ultrasound energy, coherent light such as laser, a heated fluid, a cooled fluid, or a chemical medium, an element that generates frictional heat, and a heater including an electric wire. A specific form of the energy transmission element 22 is not particularly limited.

In the present embodiment, the electrodes 24 are provided on the proximal erected sections 73 and the back contact portions 85 are provided on the distal erected sections 72. Alternatively, the electrodes 24 may be provided on the distal erected sections 72 and the back contact portions 85 may be provided on the proximal erected sections 73.

In the present embodiment, the operation knob 110, the biasing portion 120, the displacement shaft 33, and the pulling portion 35 which are capable of moving the distal end of the expandable body 21, and the housing 100 and the shaft portion 31 which are capable of moving the proximal end of the expandable body 21 function as a displacement mechanism 26 that compresses the expandable body 21 in the axial direction by relatively displacing the proximal end of the expandable body 21 with respect to the distal end of the expandable body 21 substantially along the central axis.

The expandable body 21 can be, for example, cut out from a cylinder and integrally formed. The struts that form the expandable body 21 may have, for example, a thickness of 50 μm to 500 μm and a width of 0.3 mm to 2.0 mm. Alternatively, the struts that form the expandable body 21 may have a dimension out of the range of the thickness being 50 μm to 500 μm and the width being 0.3 mm to 2.0 mm. The shape of the struts is not particularly limited, and may have, for example, a circular cross-sectional shape or a cross-sectional shape other than the circular cross-sectional shape.

The expandable body 21 can be formed of or fabricated from a metal material. As the metal material of the expandable body 21, for example, a titanium-based alloy (Ti—Ni, Ti—Pd, Ti—Nb—Sn or the like), a copper-based alloy, stainless steel, β titanium steel, and a Co—Cr alloy can be used. In accordance with an embodiment, it can be is more preferable to use an alloy or the like having a spring property, such as a nickel titanium alloy as the metal material for the expandable body 21. However, a material for a wire member of the expandable member 21 is not limited to a metal material, and may be formed of other materials.

In accordance with an embodiment, it is more preferable that the outer tube 30 and the shaft portion 31 of the elongated portion 20 are formed of or fabricated from a material having a certain degree of flexibility. Examples of such a material having a certain degree of flexibility for the outer tube and the shaft portion 31 of the elongated portion 20 can include polyolefins such as polyethylene, polypropylene, polybutene, ethylene-propylene copolymer, ethylene-vinyl acetate copolymer, ionomer, and a mixture of two or more thereof, fluororesins such as a soft polyvinyl chloride resin, polyamide, polyamide elastomer, polyester, polyester elastomer, polyurethane, and polytetrafluoroethylene, polyimide, PEEK, silicone rubber, and latex rubber.

The displacement shaft 33 and the pulling portion 35 can be formed of or fabricated from, for example, an elongated wire including a superelastic alloy such as a nickel-titanium alloy or a copper-zinc alloy, a metal material such as stainless steel, or a resin material having a relatively high rigidity. In addition, the displacement shaft 33 and the pulling portion 35 may be formed by coating the above material with polyvinyl chloride, polyethylene, polypropylene, ethylene-propylene copolymer, or a resin material such as fluororesin.

Next, the electric power supply device 190 will be described. As illustrated in FIG. 1, the electric power supply device 190 can include an electric power output unit 191, a notification unit 192, and a control unit 193.

The electric power output unit 191 is a unit that outputs electric power for performing a maintenance treatment to the connection terminal 27 of the medical device 10. The electric power output unit 191 is controlled by the control unit 193, and can output a high-frequency current for any period of time with any electric power.

The notification unit 192 is a unit that notifies the surgeon of a situation of control, a warning, or the like. The notification unit 192 can be, for example, a speaker that gives a notification with a sound or an image monitor that gives a notification with an image. A display method of the image monitor and an output method using the speaker are not particularly limited. The notification unit 192 may be an external device that is not implemented in the electric power supply device 190 and that is communicably connected to the electric power supply device 190.

The control unit 193 can include a central processing unit (CPU), a storage circuit, and an operation program. An interface such as a keyboard or a mouse may be connected to the control unit 193. The control unit 193 can be, for example, a computer.

The control unit 193 can control the electric power output unit 191 to control the output of the high-frequency current from the electric power output unit 191. The control unit 193 can cause the electric power output unit 191 to output any electric power at any period of time.

Figure 12:
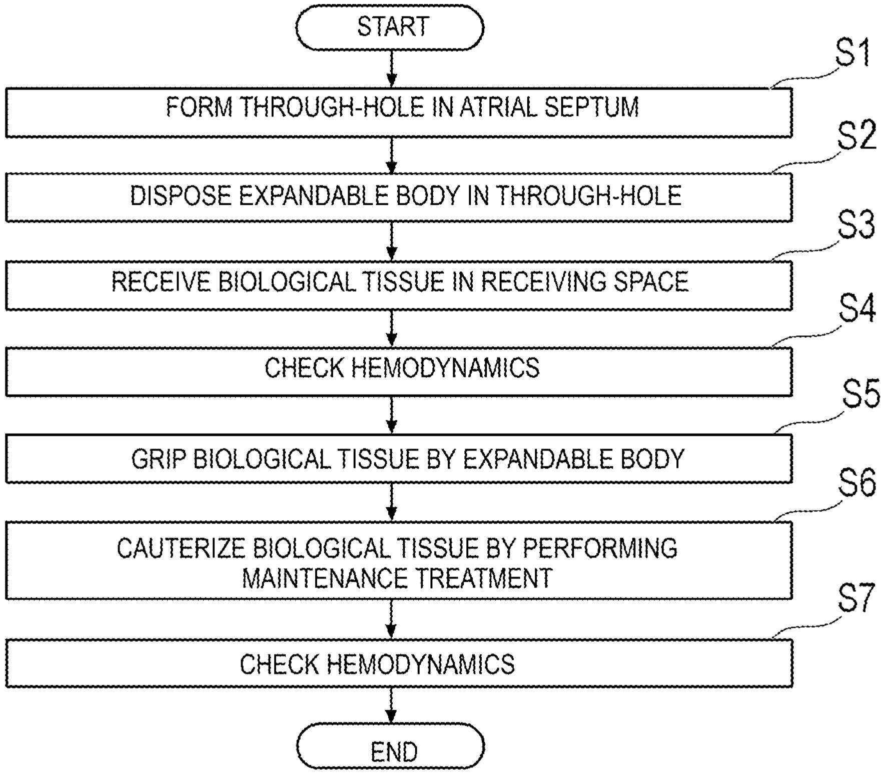
FIG. 12 is a flowchart illustrating a method for using the medical system in accordance with an embodiment of the disclosure.

Next, a method for using the medical device 10 according to the present embodiment will be described with reference to a flowchart illustrated in FIG. 12. The method is performed on a patient suffering from a heart failure (left heart failure). More specifically, as illustrated in FIG. 7, the method is a treatment method that is performed on a patient suffering from a chronic heart failure in which a myocardium of a left ventricle of the heart H is hypertrophied and increases in stiffness (hardness), resulting in an increase in blood pressure in a left atrium HLa.

The method for using the medical device 10 according to the present embodiment includes forming the through-hole Hh in the atrial septum HA (S1), disposing the expandable body 21 in the through-hole Hh (S2), receiving the biological tissue in the receiving space 74 (S3), checking hemodynamics in the vicinity of the through-hole Hh (S4), gripping the through-hole Hh by the expandable body 21 (S5), performing the maintenance treatment for maintaining the size of the through-hole Hh (S6), and checking the hemodynamics in the vicinity of the through-hole Hh after the maintenance treatment is performed (S7).

When the surgeon forms the through-hole Hh, the surgeon delivers an introducer, in which a guiding sheath and a dilator are combined together, to the vicinity of the atrial septum HA. The introducer can be delivered to, for example, a right atrium HRa via an inferior vena cava Iv. In addition, the introducer can be delivered using the guide wire 11. The surgeon can insert the guide wire 11 into the dilator, and deliver the introducer along the guide wire 11. The insertion of the introducer into a living body or the insertion of the guide wire 11 into a living body can be performed using a known method such as using an introducer for blood vessel introduction.

In S1, the surgeon causes a puncture device to penetrate through the atrial septum HA from a right atrium HRa side toward a left atrium HLa side to form the through-hole Hh in a fossa ovalis of the atrial septum HA. As the puncture device, for example, a device such as a wire having a sharp distal end can be used. The puncture device is inserted into the dilator, and is delivered to the atrial septum HA. After the guide wire 11 is removed from the dilator, instead of the guide wire 11, the puncture device can be delivered to the atrial septum HA.

Figure 8:
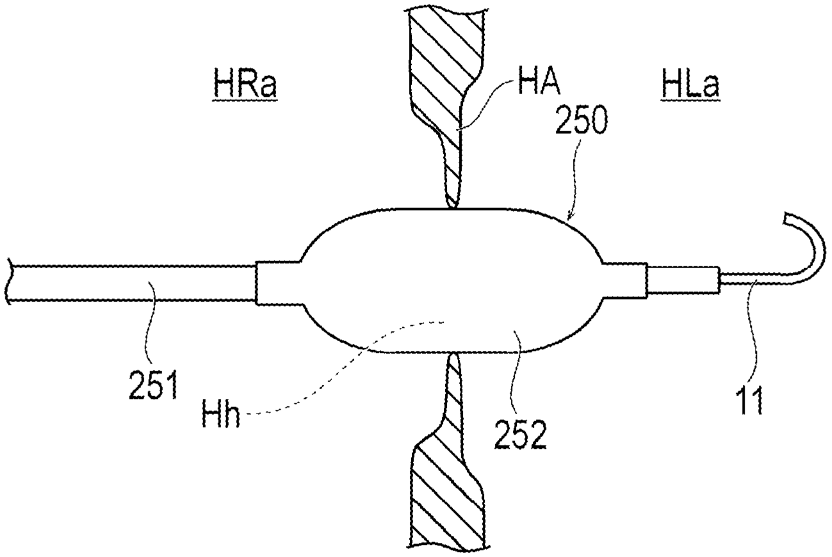
FIG. 8 is a sectional view illustrating a state in which a balloon is inserted into the atrial septum.

Next, the surgeon delivers a balloon catheter 250 to the vicinity of the atrial septum HA along the guide wire 11 inserted in advance. As illustrated in FIG. 8, the balloon catheter 250 has a balloon 252 at a distal end portion of a shaft portion 251. When the balloon 252 is disposed in the atrial septum HA, the balloon 252 is inflated in the radial direction, and the through-hole Hh is pressed to be spread or widen.

Figure 9:
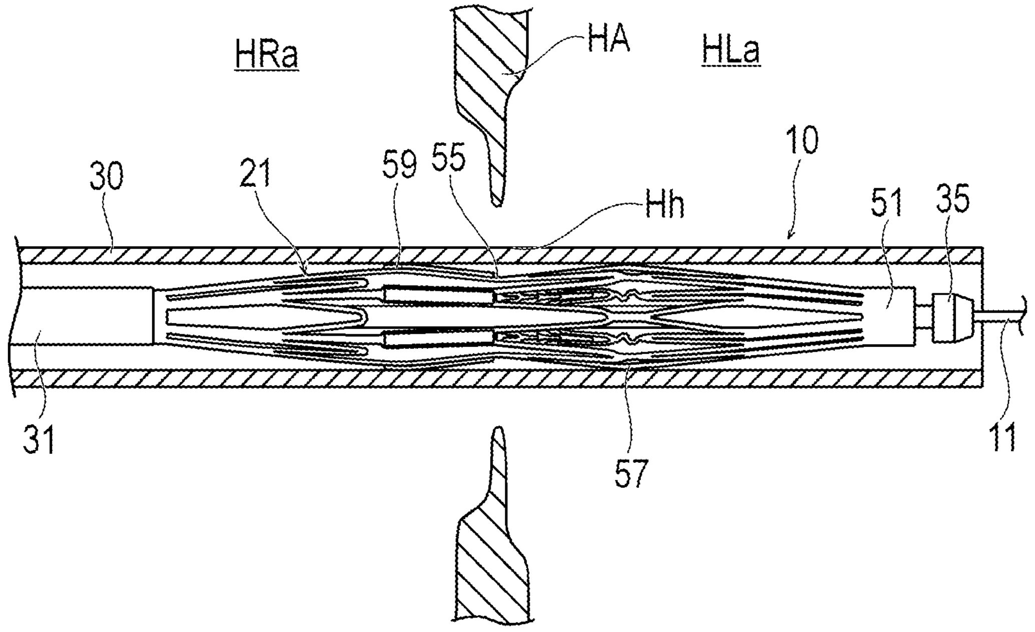
FIG. 9 is a sectional view illustrating a state in which the distal end portion of the medical device is inserted into the atrial septum.

In S2, as illustrated in FIG. 9, the medical device 10 is delivered to the vicinity of the atrial septum HA along the guide wire 11 inserted in advance. At this time, the distal end portion of the medical device 10 penetrates through the atrial septum HA and reaches the left atrium HLa. When the medical device 10 is inserted, the expandable body 21 is housed in the outer tube 30. The medical device 10 may be a device without the outer tube 30. In this case, a sheath corresponding to the outer tube 30 is separately prepared, and in S2, the sheath is delivered to the vicinity of the atrial septum HA along the guide wire 11 in advance so that a distal end portion of the sheath reaches the left atrium HLa via the through-hole Hh of the atrial septum HA. Next, the expandable body 21 of the medical device 10 is inserted into the sheath from a proximal end of the sheath, and as in FIG. 9, the distal end portion of the expandable body 21 is delivered to the left atrium HLa via the through-hole Hh of the atrial septum HA.

Figure 10:
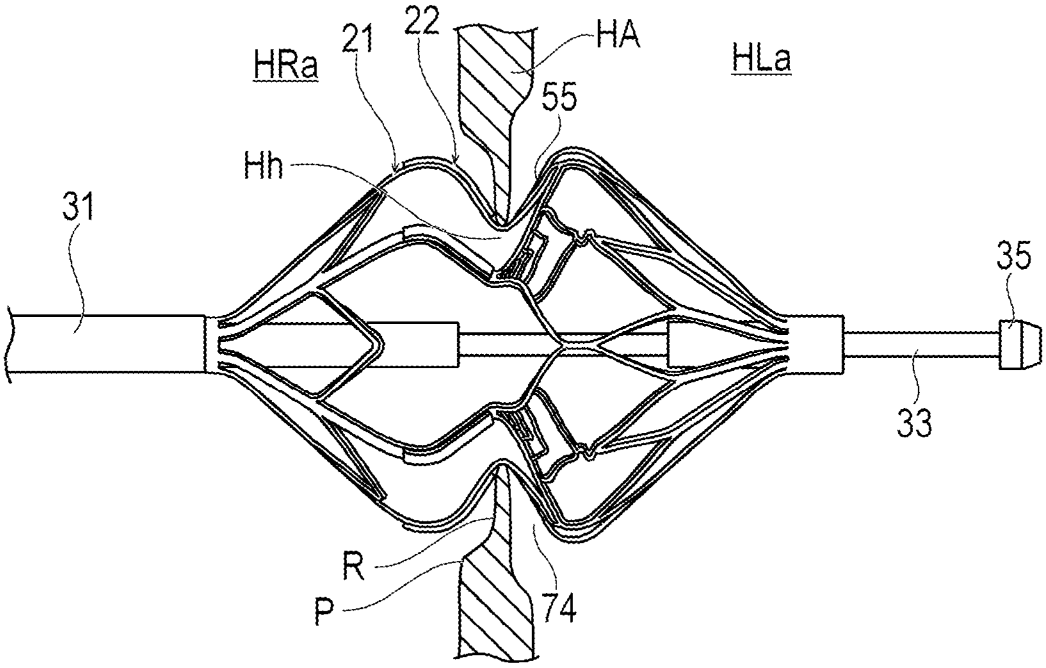
FIG. 10 is a sectional view illustrating a state in which the expandable body is disposed in the atrial septum.

Next, in S3, the expandable body 21 is exposed by moving the outer tube 30 toward the proximal side. Accordingly, as illustrated in FIG. 10, the expandable body 21 is expanded in diameter, the concave portions 55 are disposed in the through-hole Hh of the atrial septum HA, and the biological tissue surrounding the through-hole Hh is received in the receiving space 74. In this state, the operation knob 110 is located at the first position as illustrated in FIGS. 3A, 3B, and 4. The second engagement portion 142 of the lock portion 140 is located on the proximal side of the proximal surface 117B of the third engagement portion 117 in the operation knob 110. Therefore, when the operation knob 110 moves from the first position toward the proximal side due to an erroneous operation or a malfunction, the second engagement portion 142 of the lock portion 140 comes into contact with the proximal surface 117B of the third engagement portion 117 in the operation knob 110, and the movement of the operation knob 110 toward the proximal side can be prevented. Therefore, it is possible to help prevent the gripping of the biological tissue from being erroneously performed by the expandable body 21 due to an erroneous operation or a malfunction of the operation unit 23. In S1, when the through-hole Hh is pressed to be spread by the balloon 252, the through-hole Hh may not be equally pressed to be spread toward the radial direction and may have a slit shape. In this case, when the expandable body 21 is expanded in diameter and the biological tissue surrounding the through-hole Hh is received in the receiving space 74, the expandable body 21 has a shape in which the through-hole Hh expands in a direction different from a direction in which a slit extends.

When the biological tissue surrounding the through-hole Hh is received in the receiving space 74, the hemodynamics is checked in S4. As illustrated in FIG. 7, the surgeon delivers a hemodynamics checking device 200 to the right atrium HRa via the inferior vena cava Iv. As the hemodynamics checking device 200, for example, a known echo catheter can be used. The surgeon can cause a display device such as a display to display an echo image acquired by the hemodynamics checking device 200, and check the amount of blood passing through the through-hole Hh based on a display result. At this time, when the amount of the blood passing through the through-hole Hh does not reach a desired amount, the surgeon moves the outer tube 30 to the distal side to house the expandable body 21 in the outer tube 30, and then removes the expandable body 21 from the through-hole Hh together with the outer tube 30. Next, a balloon catheter including a balloon having an expanded diameter larger than that of the balloon 252 used in S1 is used and the through-hole Hh is pressed to be spread again, and the process returns to S2.

Figure 5A:
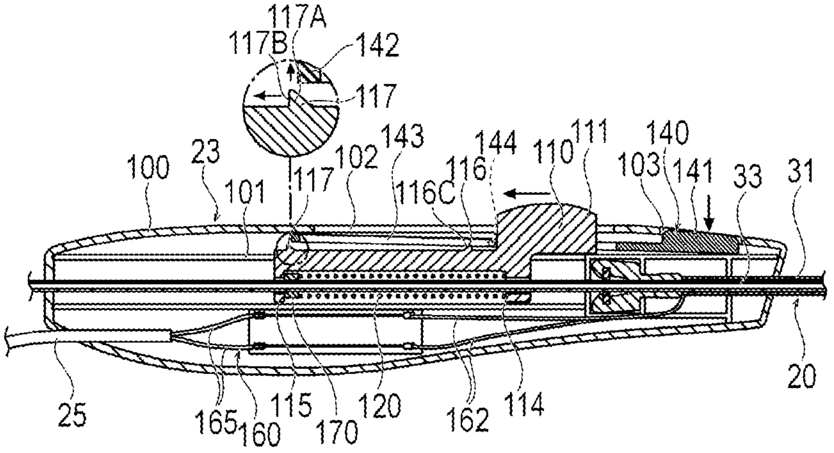
FIGS. 5A, 5B and 5C are longitudinal sectional views illustrating the inside of the operation unit.

In S5, the surgeon presses the release button 141 in a state in which the atrial septum HA is received in the receiving space 74 of the concave portions 55. Accordingly, as illustrated in FIG. 5A, the lock portion 140 pivots around the pivot shaft portion 144, and the second engagement portion 142 moves from the engagement position to the release position. Subsequently, the surgeon moves the knob body 111 toward the proximal side with respect to the housing 100. At this time, since the second engagement portion 142 is located at the release position, the proximal surface 117B of the third engagement portion 117 in the operation knob 110 is not in contact with the second engagement portion 142 of the lock portion 140. Therefore, the operation knob 110 can be moved from the first position to the proximal side.

Figure 5B:
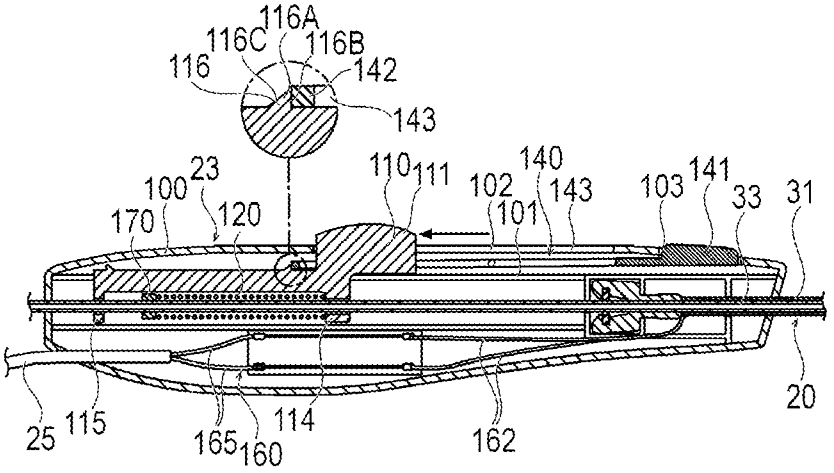

After the third engagement portion 117 exceeds the second engagement portion 142 toward the proximal side, the surgeon can release the pushing of the release button 141. Then, when the surgeon further moves the knob body 111 toward the proximal side with respect to the housing 100, the inclined surface 116C of the first engagement portion 116 comes into contact with the second engagement portion 142 of the lock portion 140. Since the inclined surface 116C can press and move the second engagement portion 142 along the inclination, as illustrated in FIG. 5B, the first engagement portion 116 exceeds the second engagement portion 142 and reaches the proximal side with respect to the second engagement portion 142. Accordingly, the distal surface 116B of the first engagement portion 116 in the operation knob 110 is disposed on a proximal side of the second engagement portion 142 in the lock portion 140.

Next, the surgeon stops the operation of moving the knob body 111 toward the proximal side. Accordingly, the operation knob 110 moves toward the distal side by a reaction force received from the expandable body 21 and/or the biasing portion 120, and the distal surface 116B of the first engagement portion 116 in the operation knob 110 engages with the second engagement portion 142 of the lock portion 140 and stops. At this time, the operation knob 110 is located at the second position.

Figure 11:
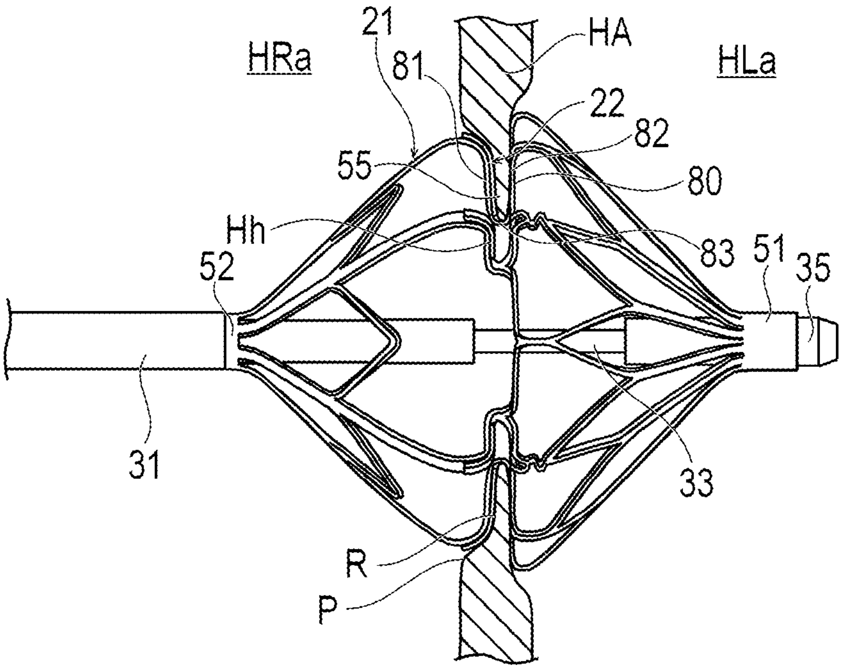
FIG. 11 is a sectional view illustrating a state in which an energy transmission element disposed in a concave portion of the expandable body is brought into close contact with a biological tissue.

According to the above-described operation, when the knob body 111 is displaced from the first position to the second position, the displacement shaft 33 is displaced from the initial position illustrated in FIGS. 3A, 3B, 4 to the compression position illustrated in FIG. 5B, and the action portion 114 provided on the operation knob 110 presses the distal end of the biasing portion 120 toward the proximal direction. Therefore, the proximal end of the biasing portion 120 presses the fixing member 170 toward the proximal direction, and the displacement shaft 33 fixed to the fixing member 170 moves toward the proximal direction. As a result, as illustrated in FIG. 11, the concave portions 55 of the expandable body 21 sandwich the biological tissue. At this time, the biological tissue surrounding the through-hole Hh is sandwiched between the energy transmission element 22 and the facing portions 82 and the biological tissue can be held (or grasped) relatively well. The operation knob 110 applies a pulling force to the displacement shaft 33 via the biasing portion 120. Therefore, it is possible to help prevent the pulling force exceeding a force that can be supported from acting on the displacement shaft 33 by the biasing portion 120. That is, when a force for sandwiching the biological tissue is likely to be excessive due to the expandable body 21, the biasing portion 120 is contracted, and the compressive force for compressing the expandable body 21 in the axial direction can be automatically adjusted. As a result, the force sandwiching the biological tissue is automatically adjusted.

Next, in S6, the surgeon performs the maintenance treatment in order to maintain the size of the through-hole Hh. In the maintenance treatment, by operating the electric power supply device 190 and applying high-frequency energy to an edge portion of the through-hole Hh through the electrodes 24, the edge portion of the through-hole Hh is cauterized (cauterized by heating) using the high-frequency energy. Based on the information obtained by the notification unit 192, the surgeon recognizes that the electric power output unit 191 is in an output mode and is in a state in which the electric power can be output, and causes the electric power output unit 191 to output electric power through an interface such as a keyboard, a mouse, or a dedicated button connected to the control unit 193.

When the biological tissue in the vicinity of the edge portion of the through-hole Hh is cauterized through the electrodes 24, a denatured portion where the biological tissue is denatured is formed in the vicinity of the edge portion. Since the biological tissue at the denatured portion is in a state in which the biological tissue loses elasticity, the shape of the through-hole Hh at the time of being pressed to be spread by the expandable body 21 can be maintained. Since the through-hole Hh is held at an appropriate size by the expandable body 21 provided with a buffer portion and is cauterized, the shape is maintained at the appropriate size. Accordingly, the through-hole Hh can be used as a shunt.

Figure 5C:
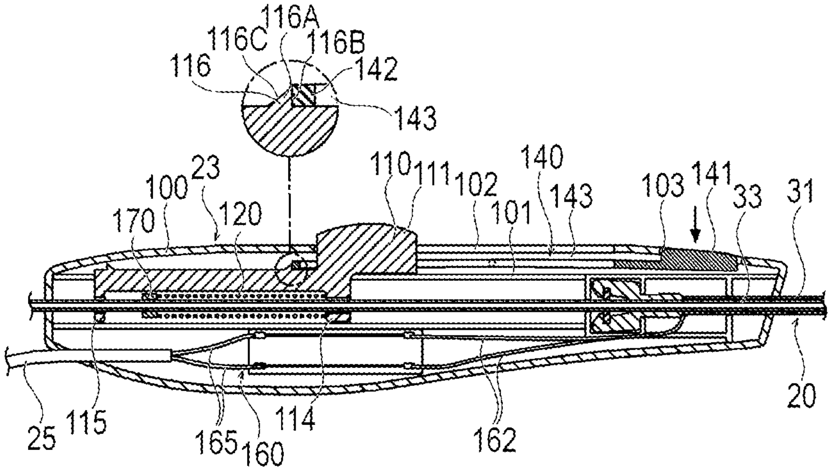

In a state in which the operation knob 110 is located at the second position, as illustrated in FIG. 5C, the first engagement portion 116 of the operation knob 110 is pressed against the second engagement portion 142 of the lock portion 140 by the reaction force of the expandable body 21 and/or the biasing portion 120. Therefore, due to a frictional force between the first engagement portion 116 and the second engagement portion 142 of the lock portion 140, the second engagement portion 142 is limited from being displaced from the engagement position at which the second engagement portion 142 is engaged with the first engagement portion 116 to the release position. Therefore, even when an erroneous operation or a malfunction such as erroneously pressing the release button 141 occurs in the state in which the operation knob 110 is located at the second position before or during the maintenance treatment, the flexible deformable portion 143 is deformed in a manner of bending, so that the displacement is absorbed and the displacement of the second engagement portion 142 engaged with the first engagement portion 116 from the engagement position to the release position is prevented.

Figure 6B:
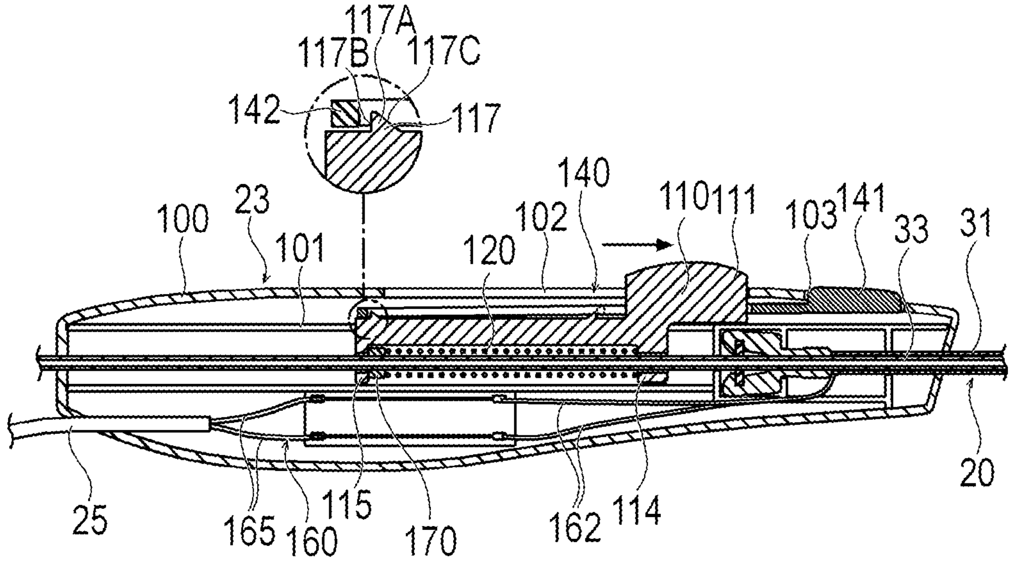

After the completion of S6, the surgeon reduces the diameter of the expandable body 21. For this purpose, first, as illustrated in FIG. 6A, the surgeon operates the operation knob 110 located at the second position and causes the operation knob 110 to be displaced to the third position at the proximal side with respect to the second position. Accordingly, since the first engagement portion 116 of the operation knob 110 is separated from the second engagement portion 142 of the lock portion 140, the frictional force stops acting between the first engagement portion 116 and the second engagement portion 142 of the lock portion 140, and the second engagement portion 142 can be displaced, to the release position, from the engagement position at which the second engagement portion 142 is engaged with the first engagement portion 116. Next, the surgeon presses the release button 141 in a state in which the operation knob 110 is maintained at the third position. Accordingly, the lock portion 140 pivots, and the second engagement portion 142 is displaced from the engagement position to the release position. In this state, as illustrated in FIG. 6B, the surgeon operates the knob body 111 and causes the operation knob 110 to be displaced to the first position at the distal side. At this time, since the second engagement portion 142 is located at the release position, the first engagement portion 116 can exceed the second engagement portion 142 and move to the distal side with respect to the second engagement portion 142. After the first engagement portion 116 exceeds the second engagement portion 142 toward the distal side, the surgeon can release the pushing of the release button 141. When the surgeon further moves the knob body 111 toward the distal side with respect to the housing 100, the inclined surface 117C of the third engagement portion 117 comes into contact with the second engagement portion 142 of the lock portion 140. Since the inclined surface 117C can press and move the second engagement portion 142 along the inclination, the third engagement portion 117 exceeds the second engagement portion 142 and reaches the distal side with respect to the second engagement portion 142. Accordingly, the proximal surface 117B of the third engagement portion 117 in the operation knob 110 is disposed on a distal side of the second engagement portion 142 in the lock portion 140. Therefore, the operation knob 110 can be displaced from the second position to the first position without being prevented from moving by the lock portion 140.

When the operation knob 110 is displaced to the first position, the compressive force acting on the expandable body 21 is released, and the expandable body 21 is in a state in which the diameter can be reduced. Next, the surgeon houses the expandable body 21 in the outer tube 30, and then removes the outer tube 30 from the through-hole Hh. Further, the surgeon removes the entire medical device 10 to the outside of the living body, and the treatment is completed.

As described above, the medical device 10 according to the present embodiment can include: the expandable body 21 that has a central axis and that is expandable and contractible in a radial direction; the elongated shaft portion 31 connected to the expandable body 21; the energy transmission element 22 provided along the expandable body 21; the housing 100 connected to a proximal end portion of the shaft portion 31; the elongated displacement shaft 33 configured to compress the expandable body 21 in an axial direction; the operation knob 110 configured to operate the displacement shaft 33 that is movable from a first position to a third position via a second position substantially along an axis of the displacement shaft 33 with respect to the housing 100; and the lock portion 140 configured to lock the operation knob 110 at the second position. The expandable body 21 includes: the concave portions 55 recessed inward in the radial direction at an intermediate portion in the axial direction; the first connection portion 54 connected to the shaft portion 31; and the second connection portion 53 facing the first connection portion 54 with the concave portions 55 interposed between the second connection portion 53 and the first connection portion 54 in the axial direction and connected to the displacement shaft 33. The concave portions 55 include, in order to define the receiving space 74 capable of receiving a biological tissue, the distal erected sections 72, the proximal erected sections 73, and the bottom sections 71 located on an innermost side in the radial direction and disposed between the distal erected sections 72 and the proximal erected sections 73. The energy transmission element 22 is disposed along any one of the distal erected sections 72 and the proximal erected sections 73 in a manner of facing the receiving space 74. The displacement shaft 33 extends from inside the housing 100 along the shaft portion 31 and is connected to the second connection portion 53, and compresses the expandable body 21 in the axial direction by relatively moving from the initial position to the compression position with respect to the shaft portion 31 along the axial direction of the expandable body 21 according to the movement of the operation knob 110 from the first position to the second position. The distal erected sections 72 and the proximal erected sections 73 grip the biological tissue by the displacement of the displacement shaft 33 from the initial position to the compression position. The operation knob 110 includes the knob body 111 that protrudes from the housing 100, and that moves and operates the operation knob 110 from the first position to the third position; the action portion 114 movably disposed in the housing 100 and connected to the proximal end portion of the displacement shaft 33, and configured to cause the displacement shaft 33 to be displaced from the initial position to the compression position according to the movement and the operation of the operation knob 110, and the first engagement portion 116 configured to move together with the action portion 114. The lock portion 140 can include: the second engagement portion 142 that is disposed in the housing 100 and that is displaceable between an engagement position at which the second engagement portion 142 is engaged with the first engagement portion 116 of the operation knob 110 located at the second position, and the release position at which the engagement with the first engagement portion 116 is released; the release button 141 that is exposed from the housing 100 and that causes the second engagement portion 142 to be displaced from the engagement position to the release position; and the flexible deformable portion 143 that connects the release button 141 and the second engagement portion 142 to each other. When the release button 141 is pressed in a state in which the operation knob 110 is located at the second position, the flexible deformable portion 143 is deformed to prevent displacement of the second engagement portion 142 engaged with the first engagement portion 116 from the engagement position to the release position, and when the release button 141 is pressed in a state in which the operation knob 110 is located at the third position, the second engagement portion 142 is displaced from the engagement position to the release position and an engagement state between the first engagement portion 116 and the second engagement portion 142 is releasable.

In the medical device 10 implemented as described above, when the operation knob 110 is not moved from the second position to the third position, even if the release button 141 is pressed, the second engagement portion 142 cannot be displaced from the engagement position to the release position, and the lock portion 140 that locks the operation knob 110 at the second position cannot be released. Therefore, the medical device 10 can reduce the release of the state in which the energy transmission element 22 is pressed against the biological tissue due to the erroneous operation or the malfunction of the operation unit 23 before or during the output of energy from the energy transmission element 22 in the state in which the expandable body 21 is compressed and the biological tissue is gripped. Therefore, it is possible to reduce a risk that a thrombus is formed by the energy transmission element 22 being exposed to blood, or that an unintended part is damaged by the energy transmission element 22.

The flexible deformable portion 143 has an elongated shape projected on a plane including the axis of the displacement shaft 33, and is pivotally disposed in the housing 100 such that an inclination amount of the flexible deformable portion 143 with respect to the axis of the displacement shaft 33 changes. The release button 141 and the second engagement portion 142 are disposed at both ends of the flexible deformable portion 143 in a direction along the axis of the displacement shaft 33. The release button 141 is pressed, so that an inclination of the flexible deformable portion 143 with respect to the axis of the displacement shaft 33 is increased, and the second engagement portion 142 is displaced from the engagement position to the release position. Accordingly, the second engagement portion 142 can be displaced from the engagement position to the release position by the inclination of the flexible deformable portion 143 with respect to the housing 100 caused by pressing the release button 141. Further, it is also possible that by flexing the flexible deformable portion 143 and absorbing the displacement generated by the release button 141 using the flexible deformable portion 143, the second engagement portion 142 is not displaced from the engagement position to the release position even if the release button 141 is pressed.

The flexible deformable portion 143 includes the pivot shaft portion 144 protruding in a direction substantially perpendicular to the axis of the displacement shaft 33 at an intermediate portion in the direction along the axis of the displacement shaft 33, and the housing 100 includes the bearing portion 104 receiving the pivot shaft portion 144. Accordingly, by rotating the flexible deformable portion 143 around the pivot shaft portion 144 received in the bearing portion 104, the operation that the release button 141 is pressed can be converted into the operation that the second engagement portion 142 is displaced from the engagement position to the release position.

The medical device 10 can include the biasing portion 120 that is elastically deformable along the axis of the displacement shaft 33 so as to bias the first engagement portion 116 of the operation knob 110 located at the second position toward the second engagement portion 142. Accordingly, since the second engagement portion 142 is pressed against the first engagement portion 116 by the biasing force of the biasing portion 120, the second engagement portion 142 can be prevented, by the frictional force, from being displaced from the engagement position to the release position.

The action portion 114 of the operation knob 110 is connected to the proximal end portion of the displacement shaft 33 via the biasing portion 120. Accordingly, since the force for gripping the biological tissue by the expandable body 21 can be appropriately adjusted by the biasing portion 120, it is possible to prevent the gripping force from becoming excessive, and to reduce damage to the biological tissue.

The operation knob 110 includes the third engagement portion 117 that engages with the second engagement portion 142 when the operation knob 110 is located at the first position to help prevent the movement of the operation knob 110 from the first position to the second position, and the engagement between the second engagement portion 142 and the third engagement portion 117 is releasable by pressing the release button 141. Accordingly, it is possible to help prevent the operation knob 110 from unintentionally moving from the first position to the second position. Therefore, the reduction in diameter of the expandable body 21, which can be reduced in the diameter, can be prevented from being hindered by the displacement shaft 33 unintentionally moving toward the proximal side, and the safety can be improved.

The first connection portion 54 of the expandable body 21 is located at a proximal side with respect to the second connection portion 53. The displacement shaft 33 compresses the expandable body 21 in the axial direction by pulling the second connection portion 53 in a proximal direction according to the movement from the initial position to the compression position located at the proximal side with respect to the initial position. The operation knob 110 causes the displacement shaft 33 to move from the initial position to the compression position according to the movement from the first position to the second position located at the proximal side with respect to the first position. The first engagement portion 116 is the first convex portion 116A that protrudes from the action portion 114 toward the direction substantially perpendicular to the axis of the displacement shaft 33 and has a distal surface. The second engagement portion 142 is a second convex portion that protrudes from the flexible deformable portion 143 toward the direction substantially perpendicular to the axis of the displacement shaft 33 to engage with the distal surface of the first convex portion 116A. Accordingly, by engaging the second convex portion provided in the lock portion 140 with the distal surface of the first convex portion 116A provided in the operation knob 110 that is moved from the first position to the second position so as to compress the expandable body 21, it is possible to rather effectively maintain a state in which the expandable body 21 is compressed.

The first convex portion 116A has the inclined surface 116C inclined such that a protruding amount from the action portion 114 gradually decreases toward a proximal end of the first convex portion 116A. The distal surface 116B of the first convex portion 116A is a surface substantially perpendicular to the axis of the displacement shaft 33. The second engagement portion 142 has a proximal surface substantially perpendicular to the axis of the displacement shaft 33 engaged with the distal surface 116B of the first convex portion 116A. Accordingly, when the operation knob 110 moves from the first position to the second position, the inclined surface 116C of the first convex portion 116A can come into contact with the second engagement portion 142 and smoothly move over the second engagement portion 142, and when the operation knob 110 reaches the second position, the distal surface 116B of the first convex portion 116A can engage with the second engagement portion 142 to help prevent the operation knob 110 from returning to the first position.

Figure 13A:
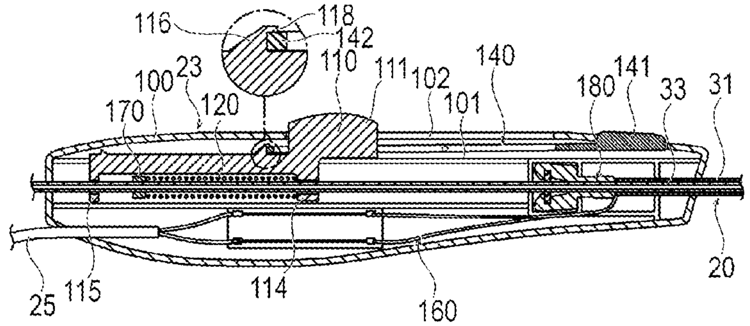
FIGS. 13A and 13B are longitudinal sectional views illustrating an inside of an operation unit according to a first modification.
Figure 13B:
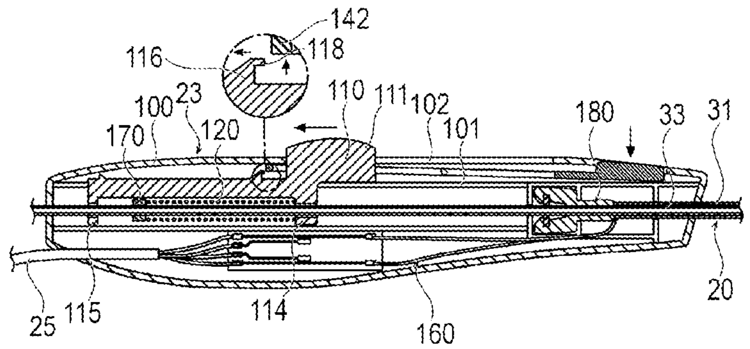

Note that the disclosure is not limited to the embodiment described above, and various modifications can be made by a person skilled in the art within a scope of the technical idea of the disclosure. For example, as in a first modification illustrated in FIGS. 13A and 13B, the operation knob 110 may include a hook portion 118 that can be engaged with the second engagement portion 142. The hook portion 118 is a convex portion that protrudes toward the distal side from a top portion of the first engagement portion 116 in a protruding direction to the second engagement portion 142. The hook portion 118 protrudes along an axis of the operation knob 110. As illustrated in FIG. 13A, when the operation knob 110 is located at the second position, the hook portion 118 is hooked on the second engagement portion 142 so as to prevent the displacement of the second engagement portion 142 from the engagement position to the release position. Further, as illustrated in FIG. 13B, when the operation knob 110 is located at the third position, the hook portion 118 can be separated from the second engagement portion 142. Accordingly, when the operation knob 110 is located at the second position, the second engagement portion 142 can be reliably prevented from being displaced from the engagement position to the release position by the hook portion 118.

Since the hook portion 118 is a convex portion protruding from the first engagement portion 116 toward the second engagement portion 142, the hook portion 118 can be firmly engaged with the second engagement portion 142, and can be easily separated from the second engagement portion 142 by the operation knob 110 moving to the third position, whereby the engagement can be released.

Figure 14A:
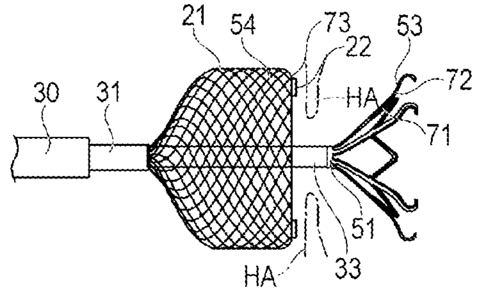
FIGS. 14A and 14B are plan views illustrating a distal end portion of a medical device according to a second modification.
Figure 14B:
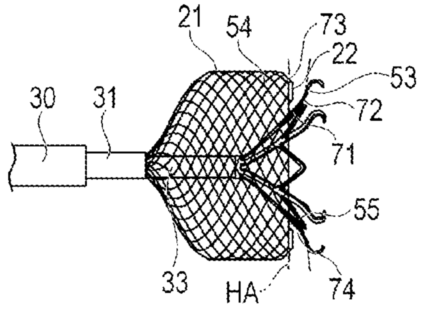

Further, as in a second modification illustrated in FIGS. 14A and 14B, the second connection portion 53 and the first connection portion 54 of the expandable body 21 may have another structure. The distal erected sections 72 and the bottom sections 71 are disposed in the second connection portion 53, and the proximal erected section 73 is disposed in the first connection portion 54. The distal erected sections 72, the bottom sections 71 and the proximal erected section 73 define the receiving space 74 of the concave portions 55. The bottom sections 71 may be disposed in the first connection portion 54. The energy transmission element 22 is disposed in the first connection portion 54, and may be disposed in the second connection portion 53. The first connection portion 54 and the second connection portion 53 are accommodated in the outer tube 30 in a state of being elastically deformed and contracted, and are expanded by an elastic expansion force (restoring force) of the first connection portion 54 and the second connection portion 53 by being exposed from the outer tube 30. The shaft portion 31 is fixed to a proximal end of the first connection portion 54, and the displacement shaft 33 is fixed to a proximal end of the second connection portion 53. The displacement shaft 33 is slidable inside the shaft portion 31. Therefore, the displacement mechanism that compresses the expandable body 21 in the axial direction is a mechanism that pulls the displacement shaft 33 toward the proximal side or that presses the shaft portion 31 toward the distal side. By operating the displacement mechanism, as illustrated in FIG. 14B, the distal erected sections 72 and the proximal erected section 73 come relatively close to each other to reduce the receiving space 74, and it is possible to grip the atrial septum HA, which is the biological tissue, between the distal erected sections 72 and the proximal erected section 73.

Further, the operation knob 110 and the displacement shaft 33 may be directly connected to each other without the biasing portion. A biasing portion may be disposed between a proximal end of the action portion 114 of the operation knob 110 and the housing 100.

The detailed description above describes embodiments of a medical device that includes an expandable body, and wherein the expandable body includes an energy transmission element that is inserted into a living body and that cauterizes a biological tissue. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device comprising:

an expandable body having a central axis and configured to be expandable and contractible in a radial direction;

an elongated shaft portion configured to be connected to the expandable body;

an energy transmission element provided along the expandable body;

a housing configured to be connected to a proximal end portion of the elongated shaft portion;

an elongated displacement shaft configured to compress the expandable body in an axial direction;

an operation knob configured to operate the elongated displacement shaft that is configured to be movable from a first position to a third position via a second position substantially along an axis of the elongated displacement shaft with respect to the housing;

a lock portion configured to lock the operation knob at the second position;

the expandable body including a concave portion recessed inward in the radial direction at an intermediate portion in the axial direction, a first connection portion connected to the elongated shaft portion, and a second connection portion facing the first connection portion with the concave portion interposed between the second connection portion and the first connection portion in the axial direction and connected to the elongated displacement shaft;

the concave portion including, in order to define a receiving space configured to receive a biological tissue, a distal erected section, a proximal erected section, and a bottom section located on an innermost side in the radial direction and disposed between the distal erected section and the proximal erected section;

the energy transmission element is disposed along one of the distal erected section and the proximal erected section in a manner of facing the receiving space;

the elongated displacement shaft extends from inside the housing along the elongated shaft portion and is connected to the second connection portion, and is configured to compress the expandable body in the axial direction by relatively moving from an initial position to a compression position with respect to the elongated shaft portion along the axial direction of the expandable body according to the movement of the operation knob from the first position to the second position;

the distal erected section and the proximal erected section configured to grip the biological tissue by displacement of the elongated displacement shaft from the initial position to the compression position;

the operation knob includes a knob body that protrudes from the housing, and configured move and operate the operation knob from the first position to the third position, an action portion configured to be movably disposed in the housing and connected to a proximal end portion of the elongated displacement shaft, and configured to cause the elongated displacement shaft to be displaced from the initial position to the compression position according to the movement and the operation of the operation knob, and a first engagement portion configured to move together with the action portion;

the lock portion including a second engagement portion that is disposed in the housing and configured to be displaceable between an engagement position at which the second engagement portion is engaged with the first engagement portion of the operation knob located at the second position, and a release position at which an engagement with the first engagement portion is released, a release button that is exposed from the housing and configured to cause the second engagement portion to be displaced from the engagement position to the release position, and a flexible deformable portion that connects the release button and the second engagement portion to each other; and when the release button is pressed in a state in which the operation knob is located at the second position, the flexible deformable portion is configured to be deformed to prevent displacement of the second engagement portion engaged with the first engagement portion from the engagement position to the release position, and when the release button is pressed in a state in which the operation knob is located at the third position, the second engagement portion is configured to be displaced from the engagement position to the release position and an engagement state between the first engagement portion and the second engagement portion is releasable.

2. The medical device according to claim 1, wherein the flexible deformable portion has an elongated shape projected on a plane including the axis of the elongated displacement shaft, and is pivotally disposed in the housing such that an inclination amount of the flexible deformable portion with respect to the axis of the elongated displacement shaft is configured to change;

the release button and the second engagement portion are disposed at both ends of the flexible deformable portion in a direction along the axis of the elongated displacement shaft; and the release button is configured to be pressed, so that an inclination of the flexible deformable portion with respect to the axis of the elongated displacement shaft is increased, and the second engagement portion is displaced from the engagement position to the release position.

3. The medical device according to claim 1, wherein the flexible deformable portion includes a pivot shaft portion protruding in a direction substantially perpendicular to the axis of the elongated displacement shaft at an intermediate portion in a direction along the axis of the elongated displacement shaft; and the housing includes a bearing portion receiving the pivot shaft portion.

4. The medical device according to claim 1, further comprising:

a biasing portion that is elastically deformable along the axis of the elongated displacement shaft so as to bias the first engagement portion of the operation knob located at the second position toward the second engagement portion.

5. The medical device according to claim 4, wherein the action portion of the operation knob is connected to the proximal end portion of the elongated displacement shaft via the biasing portion.

6. The medical device according to claim 1, wherein the operation knob includes a hook portion engageable with the second engagement portion; and when the operation knob is located at the second position, the hook portion is hooked on the second engagement portion to prevent the displacement of the second engagement portion from the engagement position to the release position, and when the operation knob is located at the third position, the hook portion is separated from the second engagement portion.

7. The medical device according to claim 6, wherein the hook portion is a convex portion protruding from the first engagement portion toward the second engagement portion.

8. The medical device according to claim 1, wherein the operation knob includes a third engagement portion that engages with the second engagement portion when the operation knob is located at the first position to prevent the movement of the operation knob from the first position to the second position, and the engagement between the second engagement portion and the third engagement portion is configured to be releasable by pressing the release button.

9. The medical device according to claim 1, wherein the first connection portion of the expandable body is located at a proximal side with respect to the second connection portion;

the elongated displacement shaft is configured to compress the expandable body in the axial direction by pulling the second connection portion in a proximal direction according to a movement from the initial position to the compression position located at the proximal side with respect to the initial position;

the operation knob is configured to cause the elongated displacement shaft to move from the initial position to the compression position according to a movement from the first position to the second position located at the proximal side with respect to the first position;

the first engagement portion is a first convex portion that protrudes from the action portion toward a direction substantially perpendicular to the axis of the elongated displacement shaft and that has a distal surface; and the second engagement portion is a second convex portion that protrudes from the flexible deformable portion toward the direction substantially perpendicular to the axis of the elongated displacement shaft to engage with the distal surface of the first convex portion.

10. The medical device according to claim 1, wherein a first convex portion has an inclined surface inclined such that a protruding amount from the action portion gradually decreases toward a proximal end of the first convex portion;

a distal surface of the first convex portion is a surface substantially perpendicular to the axis of the elongated displacement shaft; and the second engagement portion has a proximal surface substantially perpendicular to the axis of the elongated displacement shaft engaged with the distal surface of the first convex portion.

11. A treatment method to widen a through-hole in the biological tissue comprising:

disposing the expandable body of the medical device of claim 1 in the through-hole;

receiving the biological tissue in the receiving space;

checking hemodynamics in a vicinity of the through-hole;

gripping the through-hole with the expandable body;

performing a maintenance treatment for maintaining a size of the through-hole; and checking the hemodynamics in the vicinity of the through-hole after the maintenance treatment is performed.

12. A medical device comprising:

an expandable body having a central axis and configured to be expandable and contractible in a radial direction;

an elongated shaft portion configured to be connected to the expandable body;

an energy transmission element provided along the expandable body;

a housing configured to be connected to a proximal end portion of the elongated shaft portion;

an elongated displacement shaft configured to compress the expandable body in an axial direction;

an operation knob configured to operate the elongated displacement shaft that is configured to be movable from a first position to a third position via a second position substantially along an axis of the elongated displacement shaft with respect to the housing;

a lock portion configured to lock the operation knob at the second position;

the elongated displacement shaft extends from inside the housing along the elongated shaft portion and is connected to the expandable body, and is configured to compress the expandable body in the axial direction by relatively moving from an initial position to a compression position with respect to the elongated shaft portion along the axial direction of the expandable body according to the movement of the operation knob from the first position to the second position; and wherein the operation knob includes a knob body that protrudes from the housing, and configured move and operate the operation knob from the first position to the third position, an action portion configured to be movably disposed in the housing and connected to a proximal end portion of the elongated displacement shaft, and configured to cause the elongated displacement shaft to be displaced from the initial position to the compression position according to the movement and the operation of the operation knob, and a first engagement portion configured to move together with the action portion; and wherein the lock portion includes a second engagement portion that is disposed in the housing and configured to be displaceable between an engagement position at which the second engagement portion is engaged with the first engagement portion of the operation knob located at the second position, and a release position at which an engagement with the first engagement portion is released, a release button that is exposed from the housing and configured to cause the second engagement portion to be displaced from the engagement position to the release position, and a flexible deformable portion that connects the release button and the second engagement portion to each other.

13. The medical device according to claim 12, wherein when the release button is pressed in a state in which the operation knob is located at the second position, the flexible deformable portion is configured to be deformed to prevent displacement of the second engagement portion engaged with the first engagement portion from the engagement position to the release position, and when the release button is pressed in a state in which the operation knob is located at the third position, the second engagement portion is configured to be displaced from the engagement position to the release position and an engagement state between the first engagement portion and the second engagement portion is releasable.

14. The medical device according to claim 12, wherein the flexible deformable portion has an elongated shape projected on a plane including the axis of the elongated displacement shaft, and is pivotally disposed in the housing such that an inclination amount of the flexible deformable portion with respect to the axis of the elongated displacement shaft changes;

the release button and the second engagement portion are disposed at both ends of the flexible deformable portion in a direction along the axis of the elongated displacement shaft; and the release button is configured to be pressed, so that an inclination of the flexible deformable portion with respect to the axis of the elongated displacement shaft is increased, and the second engagement portion is displaced from the engagement position to the release position.

15. The medical device according to claim 12, further comprising:

a biasing portion that is elastically deformable along the axis of the elongated displacement shaft so as to bias the first engagement portion of the operation knob located at the second position toward the second engagement portion.

16. The medical device according to claim 15, wherein the action portion of the operation knob is connected to the proximal end portion of the elongated displacement shaft via the biasing portion.

17. The medical device according to claim 12, wherein the operation knob includes a hook portion engageable with the second engagement portion; and when the operation knob is located at the second position, the hook portion is hooked on the second engagement portion to prevent the displacement of the second engagement portion from the engagement position to the release position, and when the operation knob is located at the third position, the hook portion is separated from the second engagement portion.

18. A medical device comprising:

an expandable body having a central axis and configured to be expandable and contractible in a radial direction;

an elongated shaft portion configured to be connected to the expandable body;

an energy transmission element provided along the expandable body;

a housing configured to be connected to a proximal end portion of the elongated shaft portion;

an elongated displacement shaft configured to compress the expandable body in an axial direction;

an operation knob configured to operate the elongated displacement shaft that is configured to be movable from a first position to a third position via a second position substantially along an axis of the elongated displacement shaft with respect to the housing;

a lock portion configured to lock the operation knob at the second position;

the elongated displacement shaft extends from inside the housing along the elongated shaft portion and is connected to the expandable body, and is configured to compress the expandable body in the axial direction by relatively moving from an initial position to a compression position with respect to the elongated shaft portion along the axial direction of the expandable body according to the movement of the operation knob from the first position to the second position; and wherein the operation knob includes a knob body that protrudes from the housing, and configured move and operate the operation knob from the first position to the third position, an action portion configured to be movably disposed in the housing and connected to a proximal end portion of the elongated displacement shaft, and configured to cause the elongated displacement shaft to be displaced from the initial position to the compression position according to the movement and the operation of the operation knob, and a first engagement portion configured to move together with the action portion;

wherein the lock portion comprises:

a second engagement portion that is disposed in the housing and configured to be displaceable between an engagement position at which the second engagement portion is engaged with the first engagement portion of the operation knob located at the second position, and a release position at which the engagement with the first engagement portion is released; and a release button that is exposed from the housing and configured to cause the second engagement portion to be displaced from the engagement position to the release position, wherein the medical device further comprises a biasing portion elastically deformable along an axis of the elongated displacement shaft and configured to bias the first engagement portion of the operation knob located at the second position toward the second engagement portion such that a frictional force is generated between the first engagement portion and the second engagement portion, wherein, when the first engagement portion of the operation knob is disposed on a proximal side of the second engagement portion of the lock portion, the operation knob is configured to move toward a distal side by a reaction force received from the biasing portion and is configured to stop at the second position by engagement of the first engagement portion with the second engagement portion, and and wherein, by displacing the operation knob from the second position to the third position, the first engagement portion is separated from the second engagement portion such that the frictional force no longer acts.

19. The medical device according to claim 18 wherein the action portion of the operation knob is connected to the proximal end portion of the elongated displacement shaft via the biasing portion.

20. The medical device according to claim 18, wherein the operation knob includes a third engagement portion that engages with the second engagement portion when the operation knob is located at the first position to prevent the movement of the operation knob from the first position to the second position, and the engagement between the second engagement portion and the third engagement portion is configured to be releasable by pressing the release button.

* * * * *